(12) United States Patent
Yokoyama et al.

(10) Patent No.: US 8,377,573 B2
(45) Date of Patent: *Feb. 19, 2013

(54) COMPOUND HAVING SUBSTITUTED PYRIDYL GROUP AND PYRIDOINDOLE RING STRUCTURE LINKED THROUGH PHENYLENE GROUP, AND ORGANIC ELECTROLUMINESCENT DEVICE

(75) Inventors: Norimasa Yokoyama, Tsukuba (JP); Shuichi Hayashi, Tsukuba (JP); Sawa Izumi, Tsukuba (JP); Shigeru Kusano, Tsukuba (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 220 days.

This patent is subject to a terminal disclaimer.

(21) Appl. No.: 12/865,736

(22) PCT Filed: Jan. 30, 2009

(86) PCT No.: PCT/JP2009/051631

§ 371 (c)(1),
(2), (4) Date: Aug. 2, 2010

(87) PCT Pub. No.: WO2009/096549

PCT Pub. Date: Aug. 6, 2009

(65) Prior Publication Data

US 2011/0006291 A1    Jan. 13, 2011

(30) Foreign Application Priority Data

Jan. 31, 2008   (JP) .................................. 2008-020110

(51) Int. Cl.
*H01L 51/50* (2006.01)
(52) U.S. Cl. ........ 428/690; 428/917; 313/504; 313/505; 313/506; 257/40; 257/E51.05; 548/440; 546/181; 546/79; 546/81; 546/101
(58) Field of Classification Search ................. 428/690, 428/917; 313/504, 505, 506; 257/40, E51.05; 548/440; 546/18, 79, 81, 101
See application file for complete search history.

(56) References Cited

U.S. PATENT DOCUMENTS

| 2006/0251918 A1* | 11/2006 | Iwakuma et al. ............. 428/690 |
| 2009/0045726 A1 | 2/2009 | Miki et al. |
| 2011/0175079 A1 | 7/2011 | Yokoyama et al. |

FOREIGN PATENT DOCUMENTS

| EP | 2 336 130 A1 | 6/2011 |
| JP | 8 48656 | 2/1996 |
| JP | 2734341 | 1/1998 |
| JP | 3194657 | 6/2001 |
| JP | 2006 120906 | 5/2006 |
| JP | 2006 156445 | 6/2006 |
| JP | 2007 67383 | 3/2007 |
| JP | 2007 80657 | 3/2007 |
| WO | 2004 053019 | 6/2004 |
| WO | 2006 112265 | 10/2006 |
| WO | 2007 029696 | 3/2007 |
| WO | 2007 108362 | 9/2007 |
| WO | 2008 114690 | 9/2008 |
| WO | 2008 127057 | 10/2008 |

OTHER PUBLICATIONS

Extended European Search Report issued Oct. 17, 2011, in Patent Application No. 09706893.6.
"Fiftieth Meeting of Japan Society of Applied Physics and Related Societies," 28p-A-6, Lecture Preprint, p. 1413, (2003).
"Japan Society of Applied Physics", Journal of Organic Molecules/Bioelectronics Section, vol. 11, No. 1, pp. 13-19, (2000).
U.S. Appl. No. 12/867,556, filed Aug. 13, 2010, Yokoyama, et al.

* cited by examiner

*Primary Examiner* — Jennifer Chriss
*Assistant Examiner* — Gregory Clark
(74) *Attorney, Agent, or Firm* — Oblon, Spivak, McClelland, Maier & Neustadt, L.L.P.

(57) ABSTRACT

Provided is a compound having a substituted pyridyl group and a pyridoindole ring structure linked through a phenylene group, having formula (1), and an organic EL device with a pair of electrodes and at least one organic layer interposed between the electrodes, wherein the at least one organic layer having the compound:

[Chem. 1]

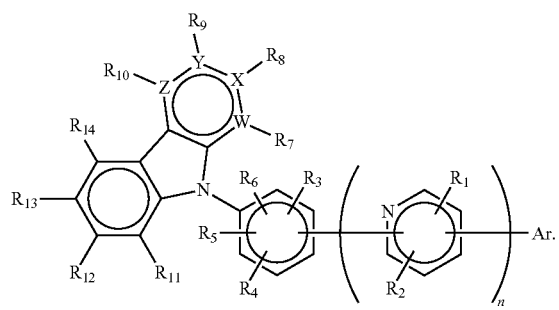

(1)

20 Claims, 2 Drawing Sheets

COMPOUND HAVING SUBSTITUTED PYRIDYL GROUP AND PYRIDOINDOLE RING STRUCTURE LINKED THROUGH PHENYLENE GROUP, AND ORGANIC ELECTROLUMINESCENT DEVICE

CROSS REFERENCE TO RELATED APPLICATIONS

The present application is the national stage of international application PCT/JP2009/051631, filed on Jan. 30, 2009, and claims the benefit of the filing date of Japanese Application No. 2008-020110, filed on Jan. 31, 2008.

TECHNICAL FIELD

The present invention relates to a compound suitable for an organic electroluminescent (EL) device which is a self-luminescent device suitable for various displaying devices and a device. More specifically, it relates to a compound having a substituted pyridyl group and a pyridoindole ring structure linked through a phenylene group and to an organic EL device using the compound.

BACKGROUND ART

Since organic EL devices are self-luminescent devices, they are bright and excellent in visibility as compared with liquid-crystalline devices and capable of giving clear display, so that the organic EL devices have been actively studied.

In 1987, C. W. Tang et al. of Eastman Kodak Company put an organic EL device using organic materials into practical use by developing a device having a multilayered structure wherein various roles are assigned to respective materials. They formed a lamination of a fluorescent material capable of transporting electrons and an organic material capable of transporting holes, so that both charges are injected into the layer of the fluorescent material to emit light, thereby achieving a high luminance of 1000 cd/m² or more at a voltage of 10 V or lower (see e.g., Patent Documents 1 and 2).

Patent Document 1: JP-A-8-48656

Patent Document 2: Japanese Patent No. 3194657

To date, many improvements have been performed for practical utilization of the organic EL devices, and high efficiency and durability have been achieved by an electroluminescent device wherein an anode, a hole-injecting layer, a hole-transporting layer, an emitting layer, an electron-transporting layer, an electron-injecting layer, and a cathode are sequentially provided on a substrate, to further segmentalize various roles (see e.g., Non-Patent Document 1).

Non-Patent Document 1: Japan Society of Applied Physics Ninth Workshop Preprint, pp. 55-61 (2001)

Moreover, for the purpose of further improvement of luminous efficiency, utilization of triplet exciton has been attempted and utilization of a phosphorescent material has been investigated (see e.g., Non-Patent Document 2).

Non-Patent Document 2: Japan Society of Applied Physics Ninth Workshop Preprint, pp. 23-31 (2001)

The emitting layer can be also prepared by doping a charge-transporting compound, generally called a host material, with a fluorescent material or a phosphorescent material. As described in the above-mentioned Workshop Preprints, the choice of the organic materials in organic EL devices remarkably affects various properties such as efficiency and durability of the devices.

In the organic EL devices, the charges injected from the both electrode are recombined in the emitting layer to attain light emission. However, since the mobility of holes is higher than the mobility of electrons, a problem of reduction in efficiency caused by a part of the holes passing through the emitting layer arises. Therefore, it is required to develop an electron-transporting material in which the mobility of electrons is high.

A representative light-emitting material, tris(8-hydroxyquinoline)aluminum (hereinafter referred to as $Alq_3$) is commonly used also as an electron-transporting material. However, since it has a work function of 5.8 eV, it cannot be considered that the material has hole-blocking capability.

As a technique to prevent the passing of a part of holes through the emitting layer and to improve probability of charge recombination in the emitting layer, there is a method of inserting a hole-blocking layer. As hole-blocking materials, there have been hitherto proposed triazole derivatives (see e.g., Patent Document 3), bathocuproine (hereinafter referred to as BCP), a mixed ligand complex of aluminum (BAlq) (see e.g., Non-Patent Document 2), and the like.

For example, as an electron-transporting material excellent in hole-blocking ability, there is proposed 3-(4-biphenylyl)-4-phenyl-5-(4-t-butylphenyl)-1,2,4-triazole (hereinafter referred to as TAZ) (see e.g., Patent Document 3).

Patent Document 3: Japanese Patent No. 2734341

Since TAZ has a work function as large as 6.6 eV and thus exhibits a high hole-blocking ability, it is used as an electron-transporting hole-blocking layer to be laminated onto the cathode side of a fluorescence-emitting layer or phosphorescence-emitting layer prepared by vacuum deposition, coating or the like, and contributes to increase the efficiency of organic EL devices (see e.g., Non-Patent Document 3).

Non-Patent Document 3: Fiftieth Meeting of Japan Society of Applied Physics and Related Societies, 28p-A-6 Lecture Preprint, p. 1413 (2003)

However, TAZ has a great problem of having low electron transport property, and it is necessary to prepare an organic EL device in combination with an electron-transporting material having a higher electron transport property (see e.g., Non-Patent Document 4).

Non-Patent Document 4: Japan Society of Applied Physics, Journal of Organic Molecules/Bioelectronics Section, Vol. 11, No. 1, pp. 13-19 (2000)

Further, BCP has a work function as large as 6.7 eV and a high hole-blocking ability, but has a low glass transition point (Tg) which is 83° C., so that it is poor in thin-film stability and thus it cannot be considered that it sufficiently functions as a hole-blocking layer.

All the materials are insufficient in thin-film stability or are insufficient in the function of blocking holes. In order to improve characteristic properties of the organic EL devices, it is desired to develop an organic compound which is excellent in electron-injection/transport performances and hole-blocking ability and is highly stable in a thin-film state.

DISCLOSURE OF THE INVENTION

Problems to be Solved by the Invention

Objects of the present invention are to provide an organic compound having excellent properties, which is excellent in electron-injection/transport performances, has hole-blocking ability and is highly stable in a thin-film state, as a material for an organic electroluminescent device having a high efficiency and a high durability, and to provide an organic electroluminescent device having a high efficiency and a high durability using the compound.

As physical properties of the organic compound to be provided by the invention, there may be mentioned (1) a good electron injection characteristic, (2) a high electron mobility, (3) an excellent hole-blocking ability, (4) good stability in a thin-film state, and (5) excellent thermal resistance. In addition, as physical properties of the organic EL device to be provided by the invention, there may be mentioned (1) a high luminous efficiency, (2) a low emission initiation voltage, and (3) a low practical driving voltage.

Means for Solving the Problems

Thus, in order to achieve the above objects, the present inventors have designed and chemically synthesized compounds having a substituted pyridyl group and a pyridoindole ring structure linked through a phenylene group, with focusing on the fact that the nitrogen atom of the pyridine ring which exhibits affinity to an electron has an ability of coordinating to a metal and is excellent in thermal resistance. The present inventors have experimentally produced various organic EL devices using the compounds, and have extensively performed property evaluation of the devices. As a result, they have accomplished the invention.

That is, the invention provides: a compound having a substituted pyridyl group and a pyridoindole ring structure linked through a phenylene group, which is represented by the general formula (1); and an organic EL device comprising a pair of electrodes and at least one organic layer interposed between the electrodes, wherein the at least one organic layer contains the compound:

[Chem. 1]

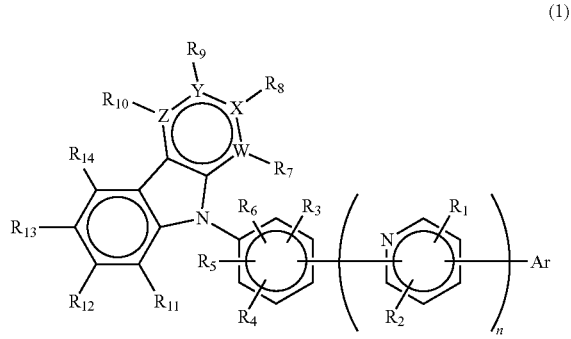

(1)

wherein Ar represents a substituted or unsubstituted aromatic hydrocarbon group, a substituted or unsubstituted aromatic heterocyclic group, or a substituted or unsubstituted condensed polycyclic aromatic group; $R_1$ to $R_{14}$ may be the same as or different from each other and each represents a hydrogen atom, a fluorine atom, a chlorine atom, a cyano group, a trifluoromethyl group, a linear or branched alkyl group having 1 to 6 carbon atoms, a substituted or unsubstituted aromatic hydrocarbon group, a substituted or unsubstituted aromatic heterocyclic group, or a substituted or unsubstituted condensed polycyclic aromatic group; n represents an integer of 1 to 3; and W, X, Y, and Z respectively represent a carbon atom or a nitrogen atom, provided that only one of W, X, Y, and Z is a nitrogen atom, and the nitrogen atom does not have the substituent of $R_7$, $R_8$, $R_9$, or $R_{10}$.

Specific examples of the "aromatic hydrocarbon group", "aromatic heterocyclic group", or "condensed polycyclic aromatic group" in the substituted or unsubstituted aromatic hydrocarbon group, the substituted or unsubstituted aromatic heterocyclic group, or the substituted or unsubstituted condensed polycyclic aromatic group, which is represented by Ar in the general formula (1), include a phenyl group, a biphenylyl group, a terphenylyl group, a tetrakisphenyl group, a styryl group, a naphthyl group, an anthryl group, an acenaphthenyl group, a fluorenyl group, a phenanthryl group, an indenyl group, a pyrenyl group, a pyrimidyl group, a furanyl group, a pyronyl group, a thiophenyl group, a quinolyl group, an isoquinolyl group, a benzofuranyl group, a benzothiophenyl group, an indolyl group, a carbazolyl group, a benzoxazolyl group, a benzothiazolyl group, a quinoxalyl group, a benzoimidazolyl group, a pyrazolyl group, a dibenzofuranyl group, a dibenzothiophenyl group, a naphthyridinyl group, a phenanthrolinyl group, and an acridinyl group.

The "substituent" in the substituted aromatic hydrocarbon group, the substituted aromatic heterocyclic group, or the substituted condensed polycyclic aromatic group, represented by Ar in the general formula (1) specifically includes groups such as a fluorine atom, a chlorine atom, a cyano group, a hydroxyl group, a nitro group, an alkyl group, a cycloalkyl group, an alkoxy group, an amino group, a phenyl group, a naphthyl group, an anthryl group, a styryl group, a pyridyl group, a pyridoindolyl group, a quinolyl group, and a benzothiazolyl group. These substituents may be further substituted.

Specific examples of the "aromatic hydrocarbon group", "aromatic heterocyclic group", or "condensed polycyclic aromatic group" in the substituted or unsubstituted aromatic hydrocarbon group, the substituted or unsubstituted aromatic heterocyclic group, or the substituted or unsubstituted condensed polycyclic aromatic group, represented by $R_1$ to $R_{14}$ in the general formula (1) include a phenyl group, a biphenylyl group, a terphenylyl group, a tetrakisphenyl group, a styryl group, a naphthyl group, an anthryl group, an acenaphthenyl group, a fluorenyl group, a phenanthryl group, an indenyl group, a pyrenyl group, pyridyl group a pyrimidyl group, a furanyl group, a pyronyl group, a thiophenyl group, a quinolyl group, an isoquinolyl group, a benzofuranyl group, a benzothiophenyl group, an indolyl group, a carbazolyl group, a benzoxazolyl group, a benzothiazolyl group, a quinoxalyl group, a benzoimidazolyl group, a pyrazolyl group, a dibenzofuranyl group, a dibenzothiophenyl group, a naphthyridinyl group, a phenanthrolinyl group, and an acridinyl group.

The "substituent" in the substituted aromatic hydrocarbon group, the substituted aromatic heterocyclic group, or the substituted condensed polycyclic aromatic group, represented by $R_1$ to $R_{14}$ in the general formula (1) specifically includes a fluorine atom, a chlorine atom, a trifluoromethyl group, a linear or branched alkyl group having 1 to 6 carbon atoms, a phenyl group, a biphenylyl group, a terphenylyl group, a tetrakisphenyl group, a styryl group, a naphthyl group, a fluorenyl group, a phenanthryl group, an indenyl group, and a pyrenyl group. These substituents may be further substituted.

The compound having a substituted pyridyl group and a pyridoindole ring structure linked through a phenylene group, which is represented by the general formula (1) of the invention, is a novel compound, provides high electron mobility as compared with conventional electron-transporting materials, has an excellent hole-blocking ability, and is stable in a thin-film state.

The compound having a substituted pyridyl group and a pyridoindole ring structure linked through a phenylene group, which is represented by the general formula (1) of the invention, can be used as a constituent material for an electron-transporting layer of an organic EL device. The use of the material exhibiting a higher electron injection/mobile rate as compared with conventional materials provides effects of improving electron transport efficiency from the electron-transporting layer to an emitting layer to enhance luminous efficiency and also lowering a driving voltage to enhance durability of the organic EL device.

The compound having a substituted pyridyl group and a pyridoindole ring structure linked through a phenylene group, which is represented by the general formula (1) of the invention, can be also used as a constituent material for a hole-blocking layer of an organic EL device. The use of the material excellent in hole-blocking ability and also excellent in electron transport property as compared with conventional materials and having high stability in a thin-film state provides effects of lowering a driving voltage, improving current resistance, and enhancing maximum emission luminance of the organic EL device, while exhibiting a high luminous efficiency.

The compound having a substituted pyridyl group and a pyridoindole ring structure linked through a phenylene group, which is represented by the general formula (1) of the invention, can be also used as a constituent material for an emitting layer of an organic EL device. The use of an emitting layer prepared by using the material of the invention excellent in electron transport property as compared with conventional materials and having a wide band-gap as a host material for the emitting layer and making a fluorescent material or a phosphorescent material, called a dopant, carried thereon provides an effect of realizing an organic EL device exhibiting a lowered driving voltage and having an improved luminous efficiency.

The organic EL device of the invention is prepared by using a compound having a substituted pyridyl group and a pyridoindole ring structure linked through a phenylene group, which compound exhibits high electron mobility as compared with a conventional electron-transporting material, has an excellent hole-blocking ability and is stable in a thin-film state. Therefore, it becomes possible to realize high efficiency and high durability.

ADVANTAGEOUS EFFECTS

The compound having a substituted pyridyl group and a pyridoindole ring structure linked through a phenylene group of the invention is useful as a constituent material for an electron-transporting layer, a hole-blocking layer, or an emitting layer of an organic EL device, and the compound has an excellent hole-blocking ability, is stable in a thin-film state, and has excellent thermal resistance. The organic EL device of the invention has a high luminous efficiency, whereby the practical driving voltage of the device can be lowered. By lowering the light emission initiation voltage, the durability can be improved.

DESCRIPTION OF REFERENCE NUMERALS AND SIGNS

Figure 1:
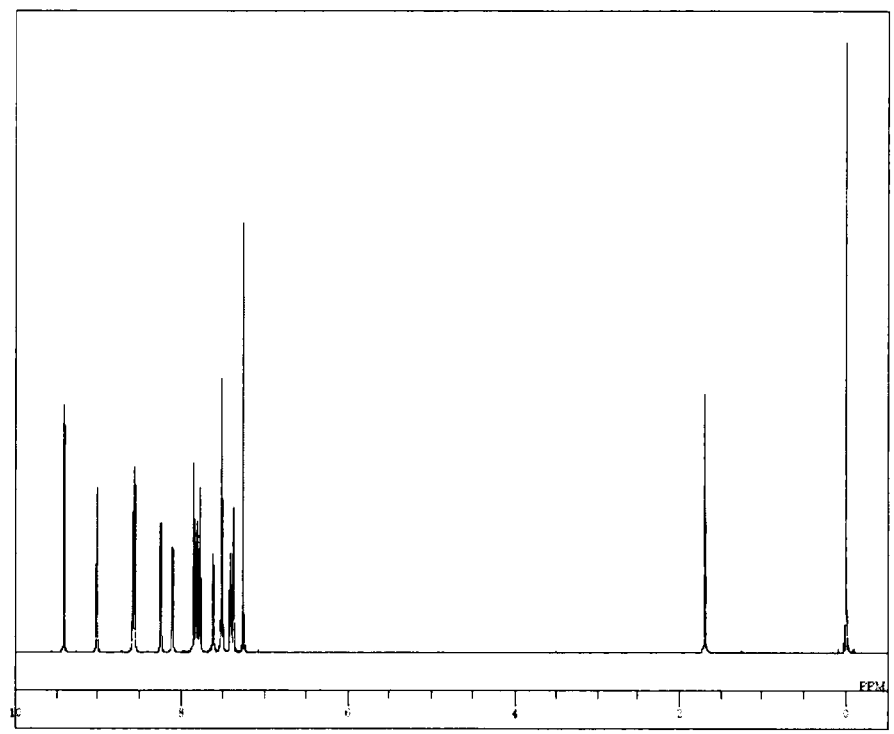
FIG. 1 is a 1H-NMR chart of the compound (Compound 99) of Invention Example 1.

1: Glass substrate
2: Transparent anode
3: Hole-injecting layer
4: Hole-transporting layer
5: Emitting layer
6: Hole-blocking layer
7: Electron-transporting layer
8: Electron-injecting layer
9: Cathode

BEST MODE FOR CARRYING OUT THE INVENTION

The compound having a substituted pyridyl group and a pyridoindole ring structure linked through a phenylene group of the invention is a novel compound, and the compound can be synthesized, for example, by the following method. A halogenophenylene pyridoindole ring structure can be synthesized by first subjecting a corresponding halogenoanilinopyridine to a cyclization reaction by a palladium catalyst to synthesize a pyridoindole ring (see e.g., Non-Patent Document 5) and then condensing it with various halogenophenylenes. Further, a boric ester can be synthesized by subjecting the corresponding halogenophenylene pyridoindole ring structure to a boric esterification reaction by a palladium catalyst. In addition, a compound having a substituted pyridyl group and a pyridoindole ring structure linked through a phenylene group can be synthesized by subjecting a corresponding dihalogenobipyridine to a condensation reaction with a tin reagent to synthesize a dihalogenobipyridyl group (see e.g., Non-Patent Document 6), and then condensing it with the boric ester.

Non-Patent Document 5: J. Chem. Soc., Perkin Trans. 1, p. 1505 (1999)

Non-Patent Document 6: J. Org. Chem., 67, p. 443 (2002)

Among the compounds having a substituted pyridyl group and a pyridoindole ring structure linked through a phenylene group, which is represented by the general formula (1), specific examples of preferred compounds are shown below, but the invention is not limited to these compounds.

[Chem. 2]
(Compound 2)
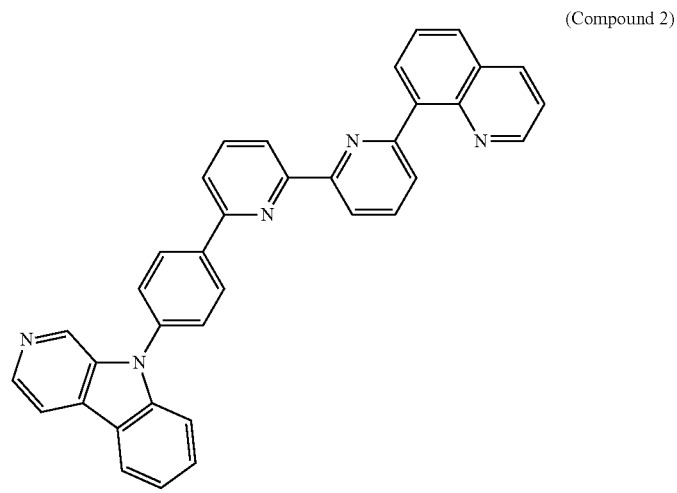
[Chem. 3]
(Compound 3)
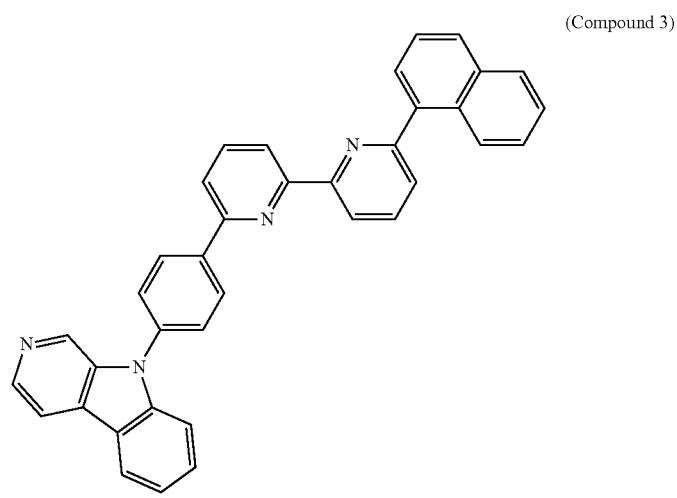
[Chem. 4]
(Compound 4)
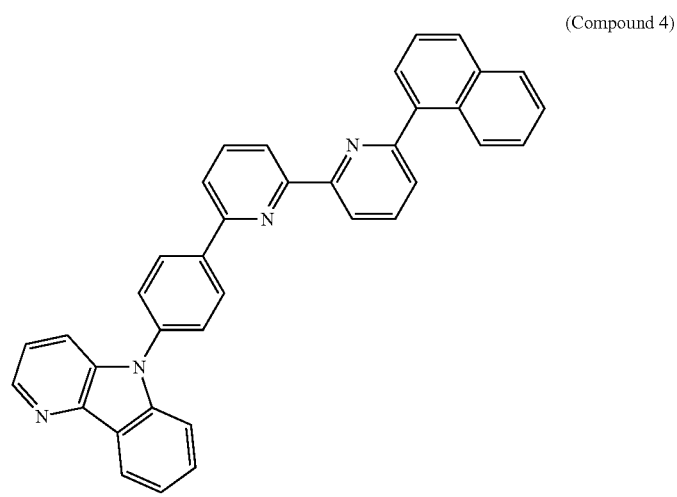

-continued
[Chem. 5]
(Compound 5)
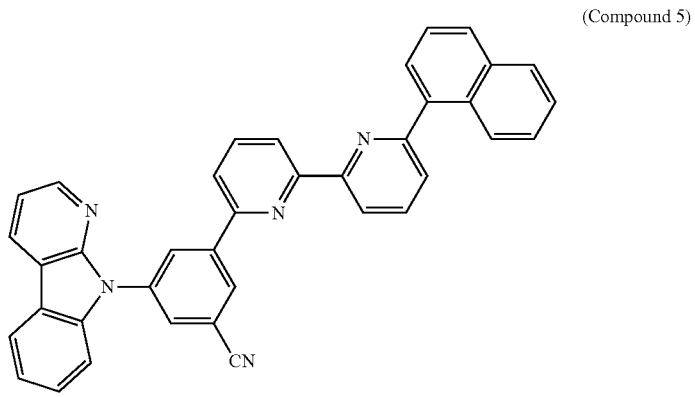
[Chem. 6]
(Compound 6)
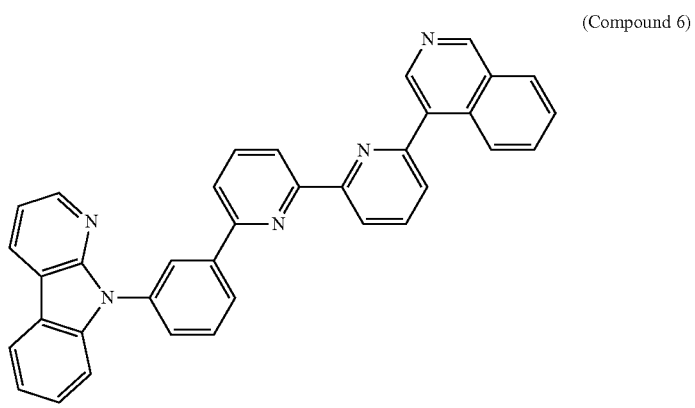
[Chem. 7]
(Compound 7)
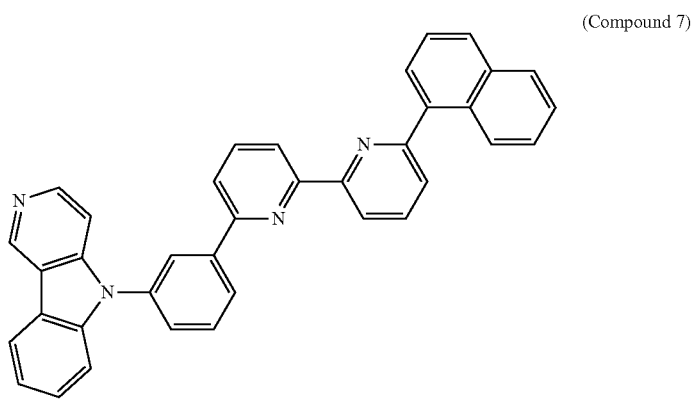

-continued
[Chem. 8]
(Compound 8)
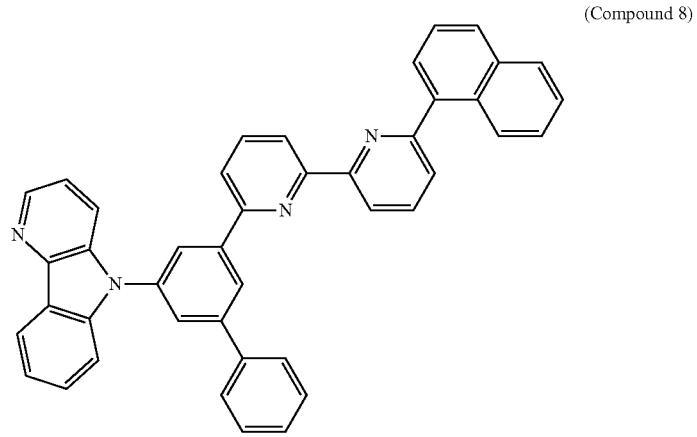
[Chem. 9]
(Compound 9)
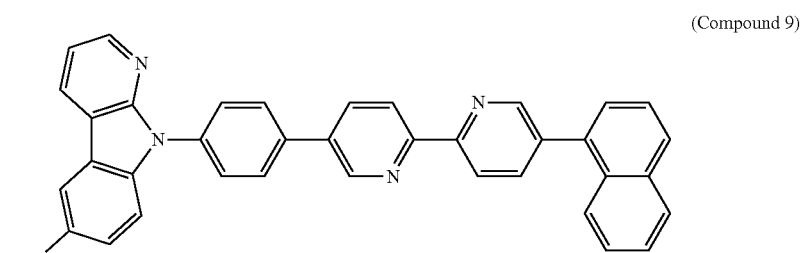
[Chem. 10]
(Compound 10)
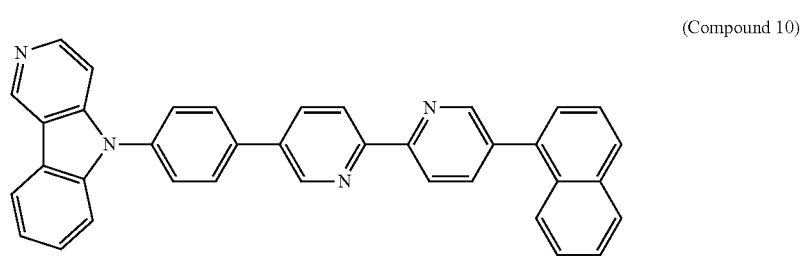
[Chem. 11]
(Compound 11)
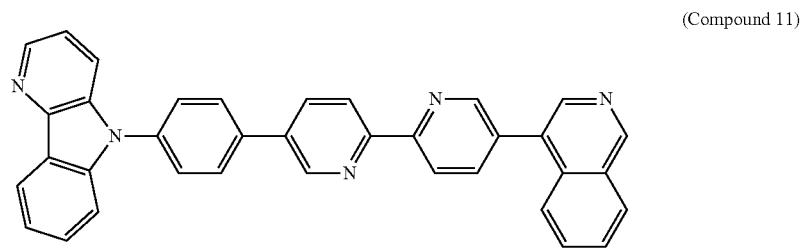
[Chem. 12]
(Compound 12)
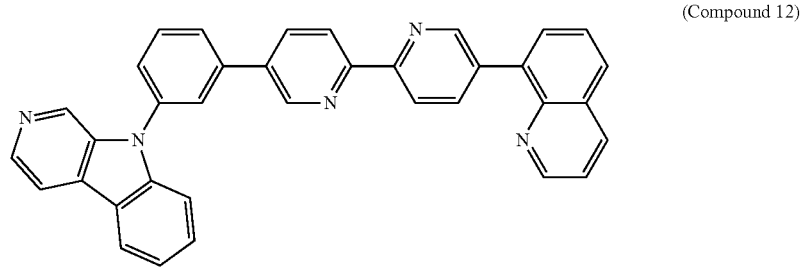

-continued
[Chem. 13]
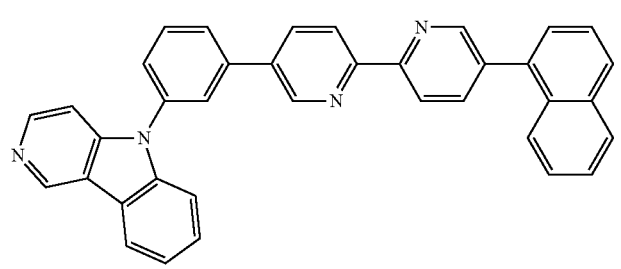
(Compound 13)
[Chem. 14]
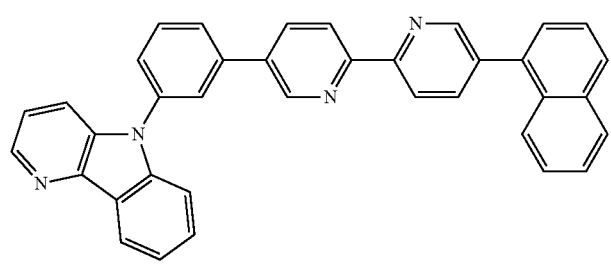
(Compound 14)
[Chem. 15]
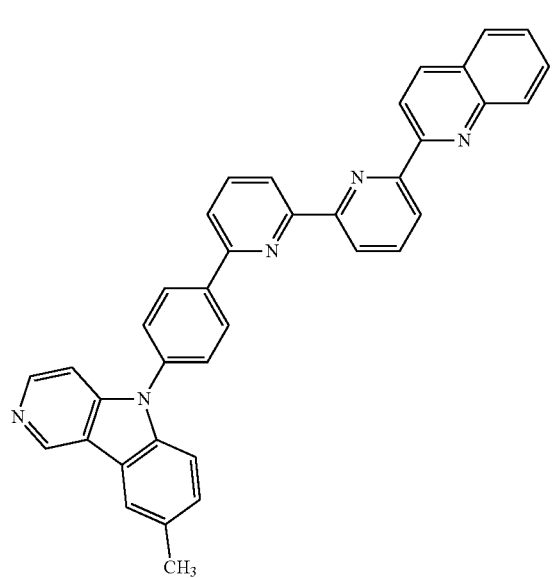
(Compound 15)

(Compound 16)
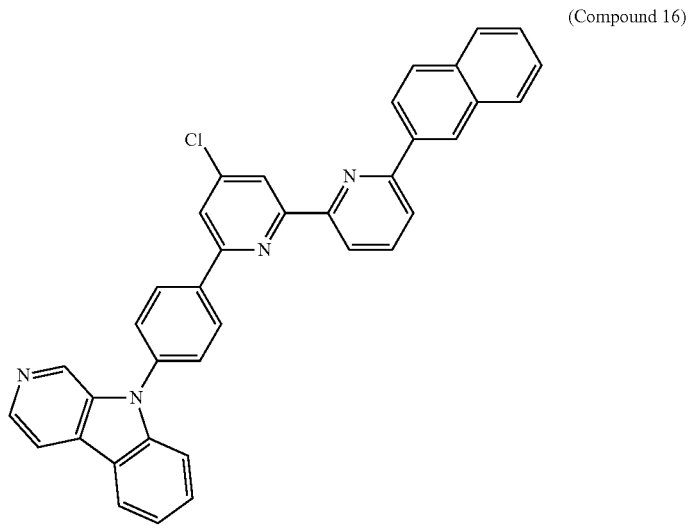
(Compound 17)
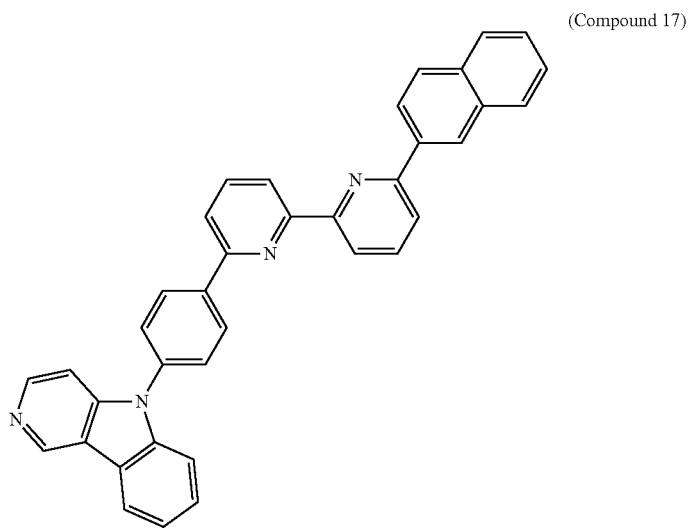
(Compound 18)
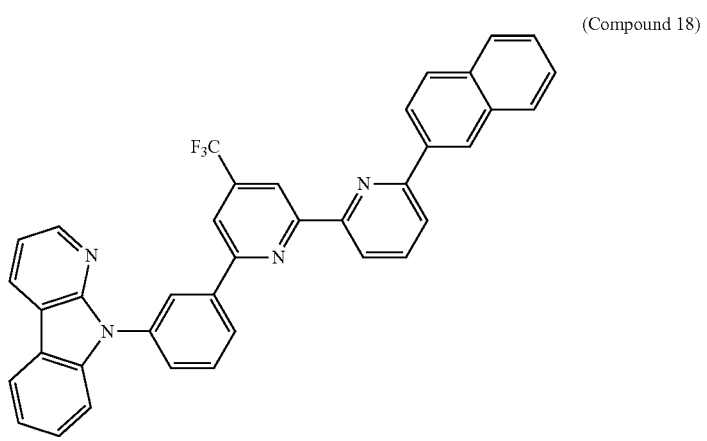

-continued
(Compound 19)
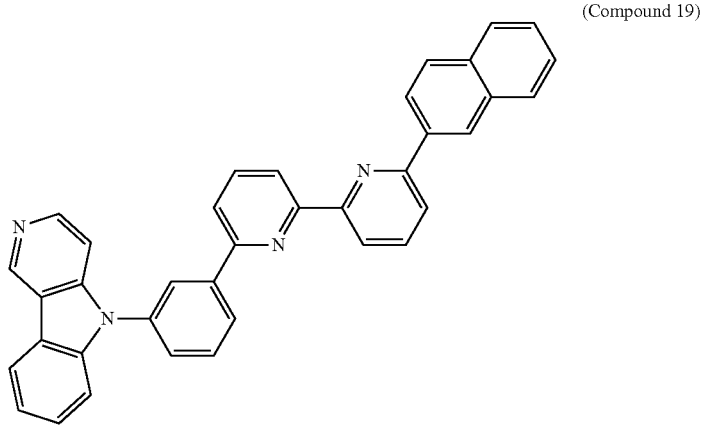
(Compound 20)
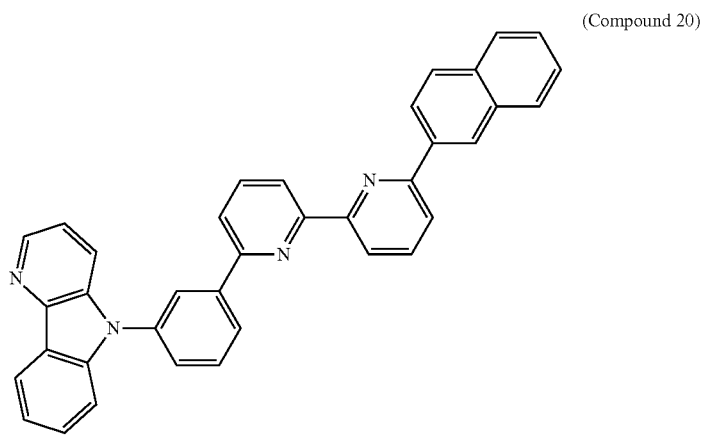
(Compound 21)
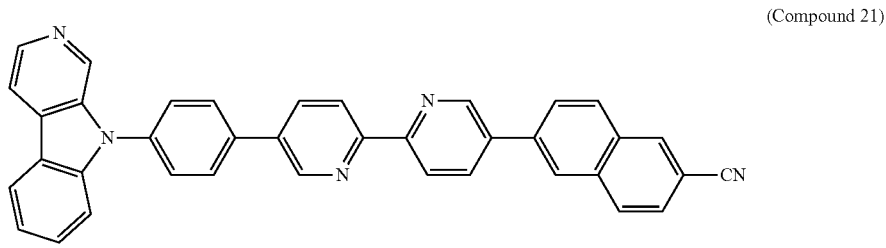
(Compound 22)
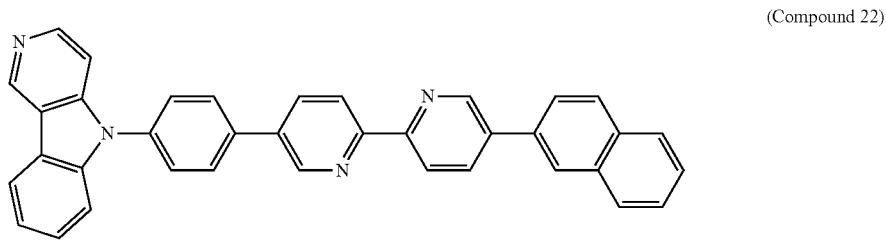

-continued
[Chem. 23]
(Compound 23)
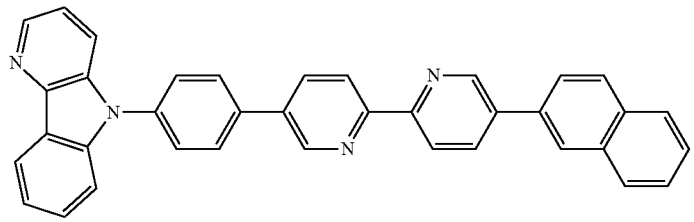
[Chem. 24]
(Compound 24)
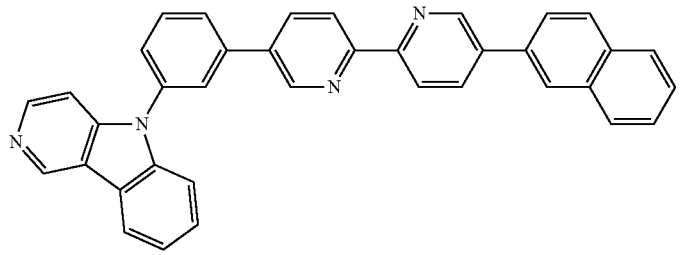
[Chem. 25]
(Compound 25)
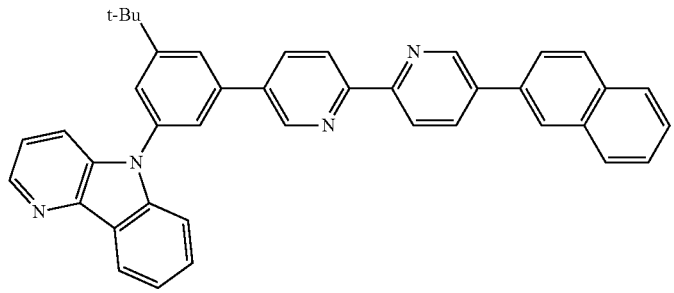
[Chem. 26]
(Compound 26)
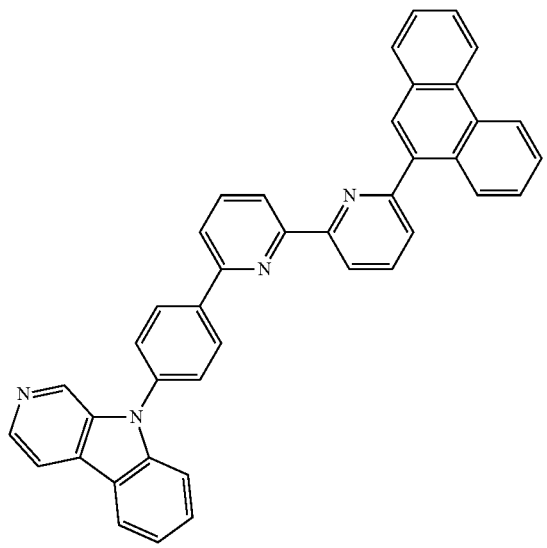

[Chem. 27]
(Compound 27)
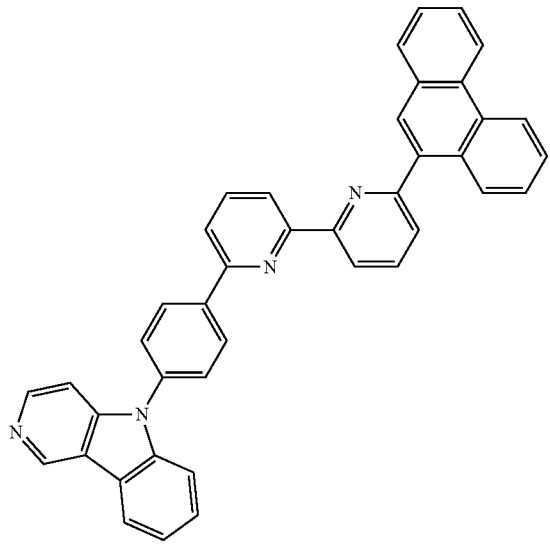
[Chem. 28]
(Compound 28)
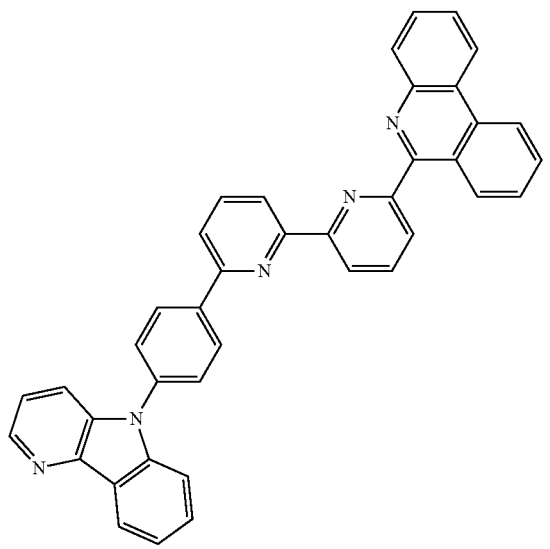

-continued
[Chem. 29]
(Compound 29)
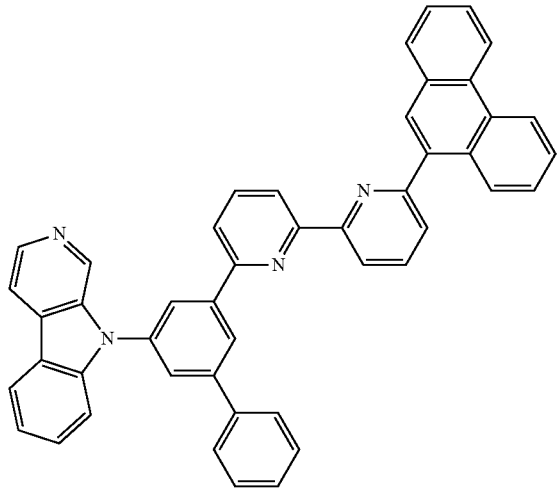
[Chem. 30]
(Compound 30)
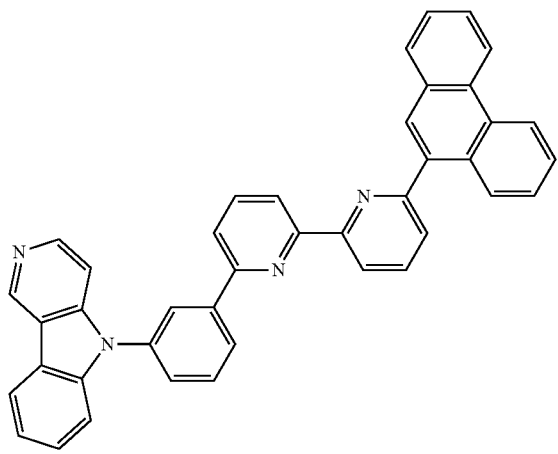
[Chem. 31]
(Compound 31)
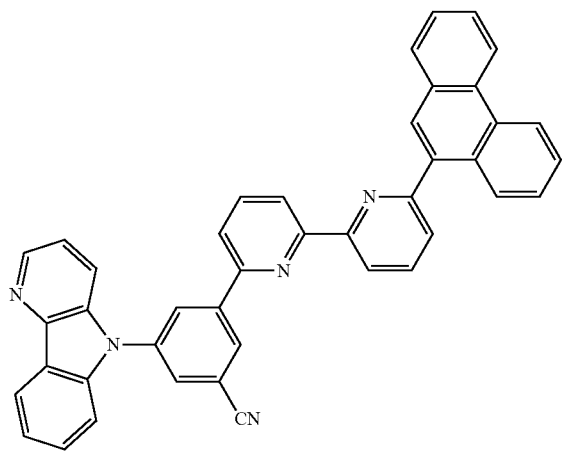

[Chem. 32]
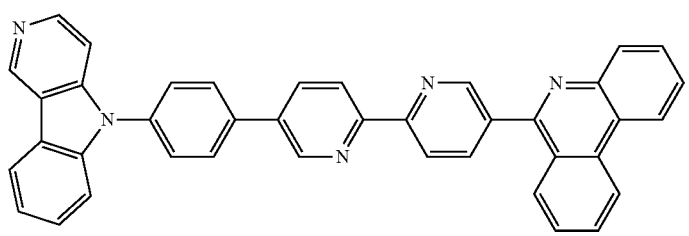
(Compound 32)
[Chem. 33]
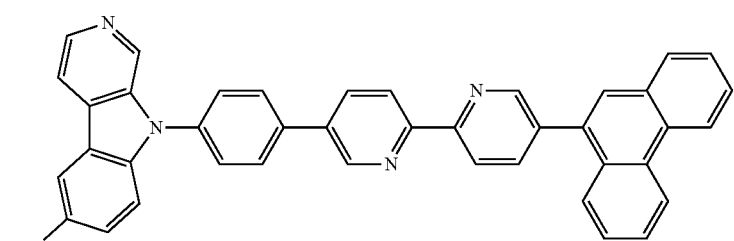
(Compound 33)
[Chem. 34]
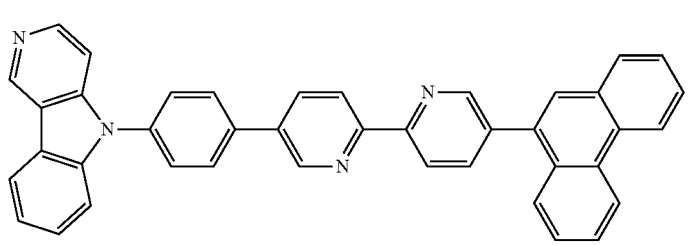
(Compound 34)
[Chem. 35]
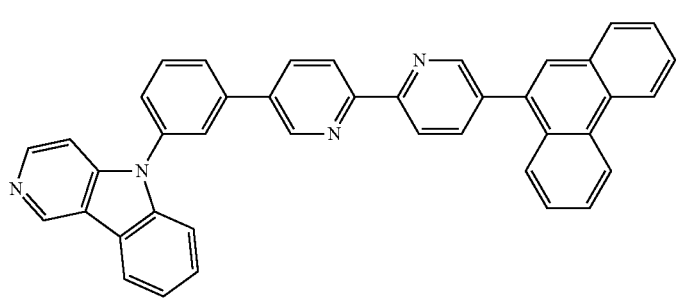
(Compound 35)
[Chem. 36]
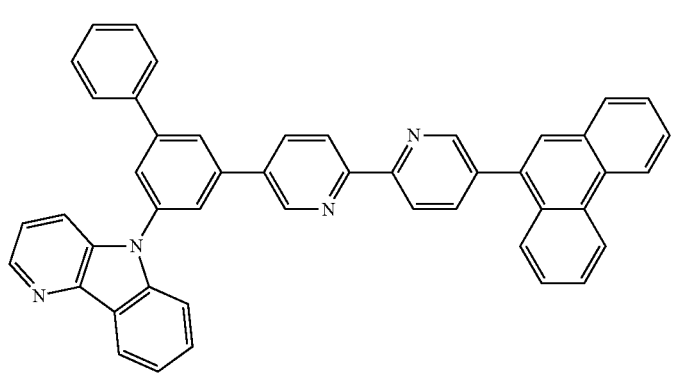
(Compound 36)

-continued
[Chem. 37]
(Compound 37)
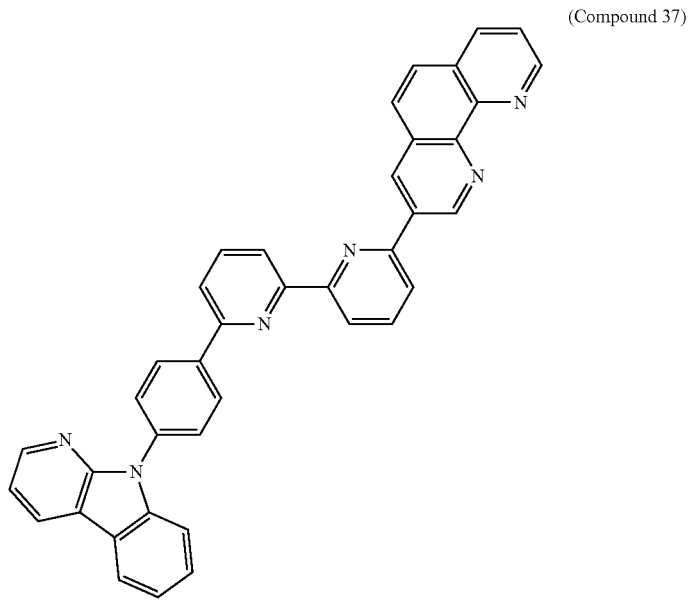
[Chem. 38]
(Compound 38)
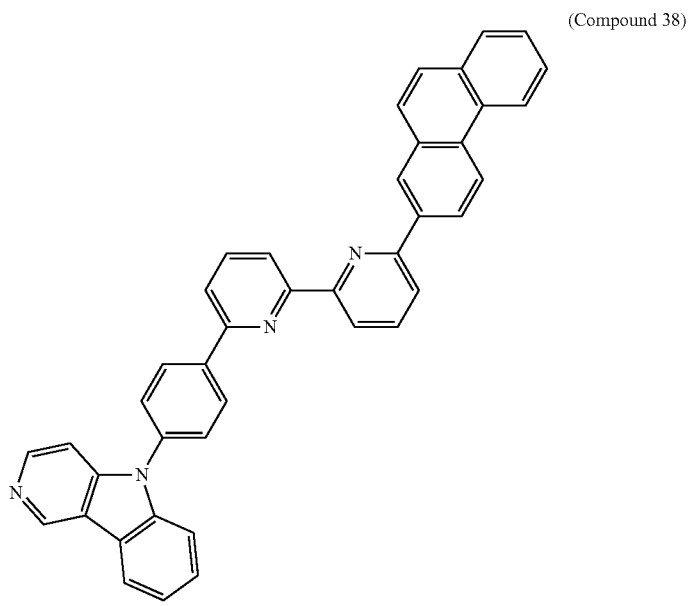

[Chem. 39]
(Compound 39)
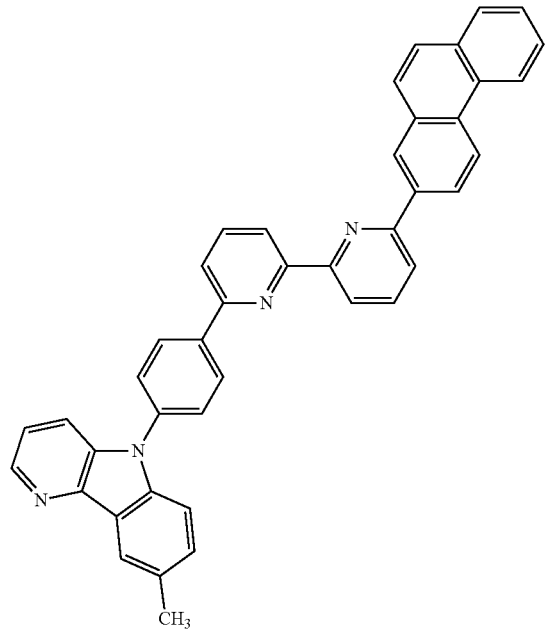
[Chem. 40]
(Compound 40)
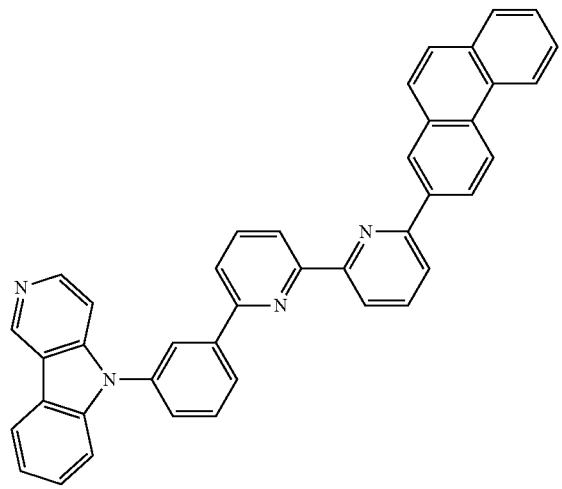

-continued
[Chem. 41]
(Compound 41)
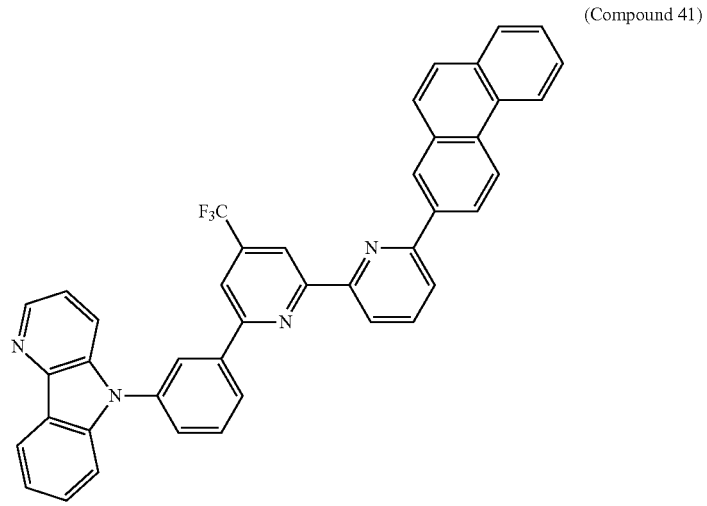
[Chem. 42]
(Compound 42)
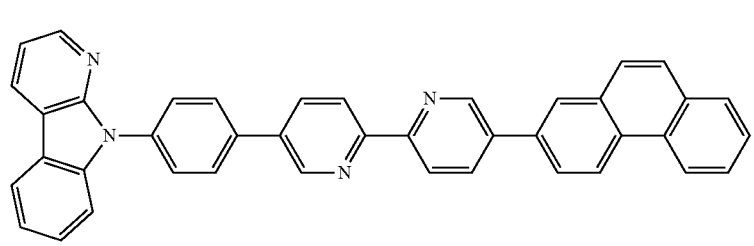
[Chem. 43]
(Compound 43)
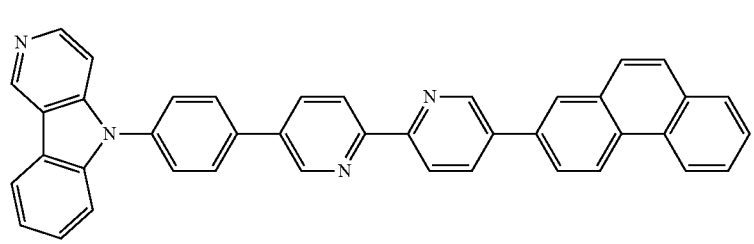
[Chem. 44]
(Compound 44)
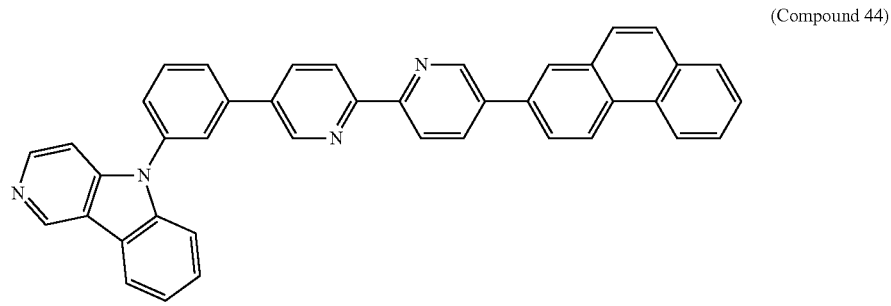

[Chem. 45]
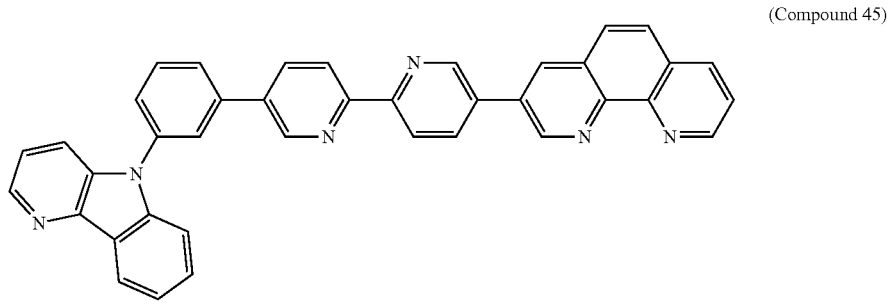
(Compound 45)
[Chem. 46]
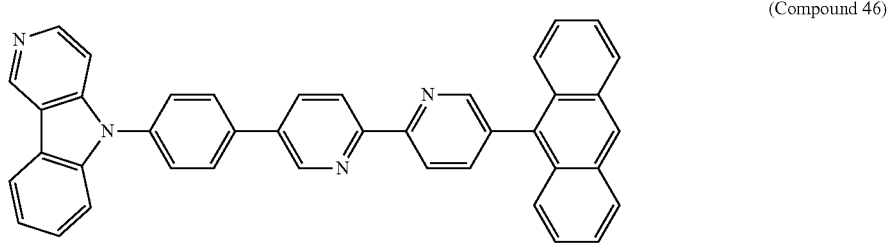
(Compound 46)
[Chem. 47]
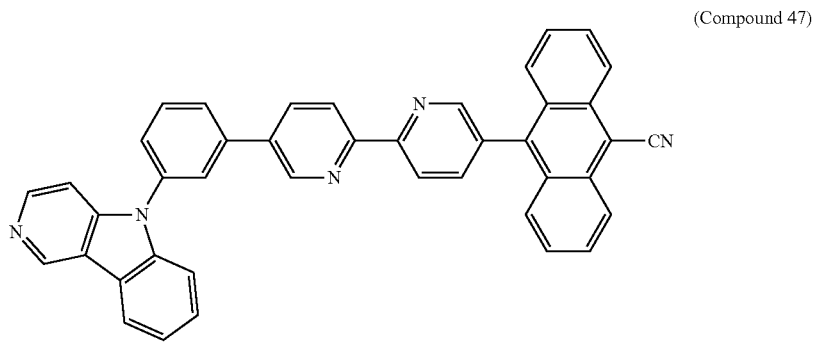
(Compound 47)
[Chem. 48]
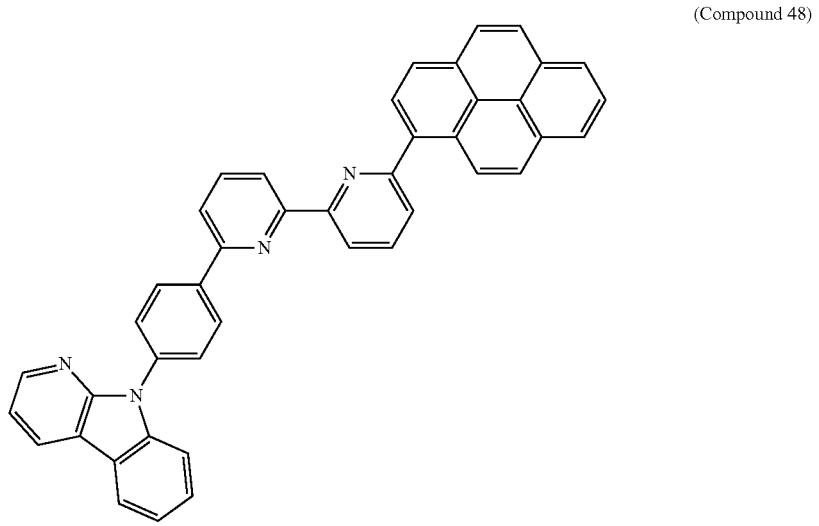
(Compound 48)

[Chem. 49]
(Compound 49)
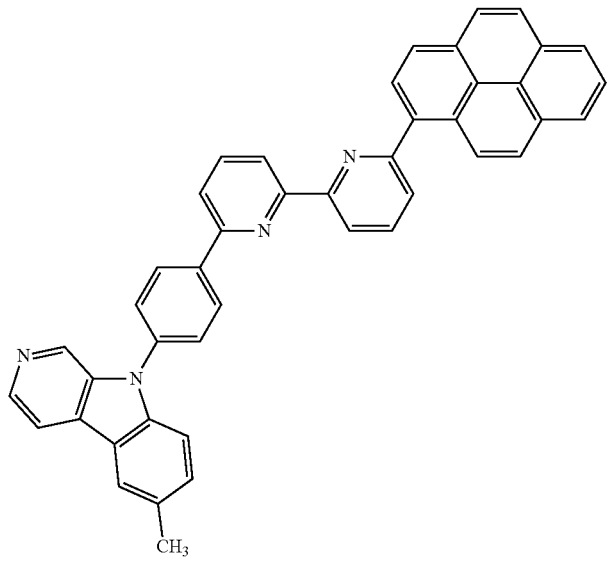
[Chem. 50]
(Compound 50)
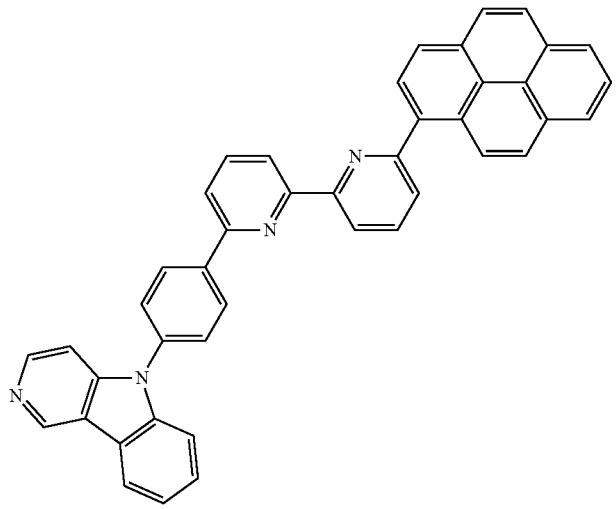

[Chem. 51]
(Compound 51)
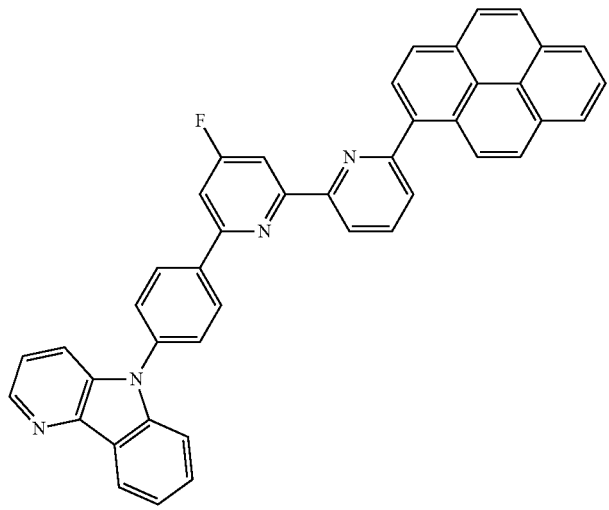
[Chem. 52]
(Compound 52)
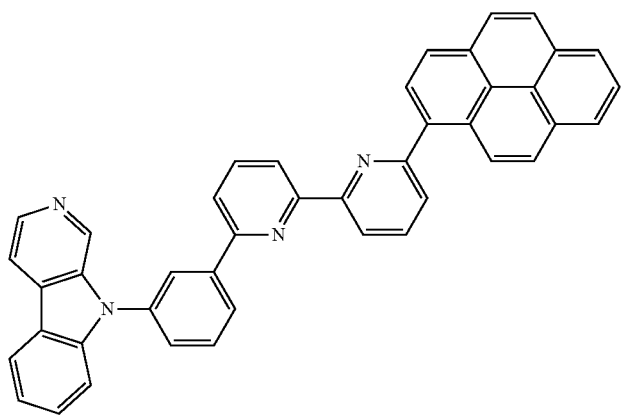
[Chem. 53]
(Compound 53)
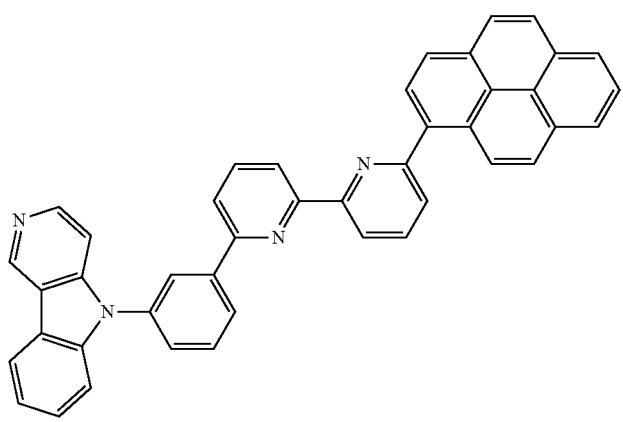

-continued
[Chem. 54]
(Compound 54)
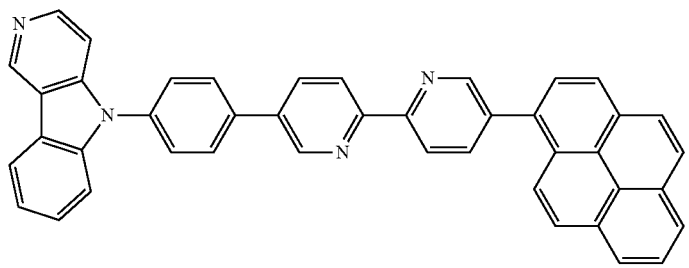
[Chem. 55]
(Compound 55)
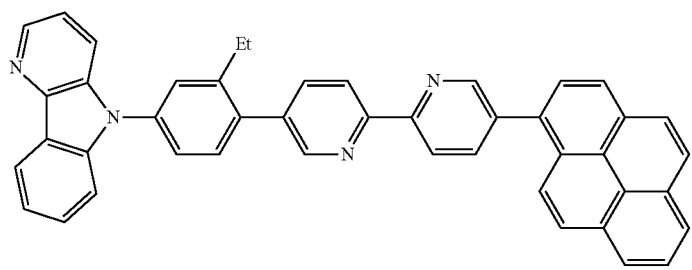
[Chem. 56]
(Compound 56)
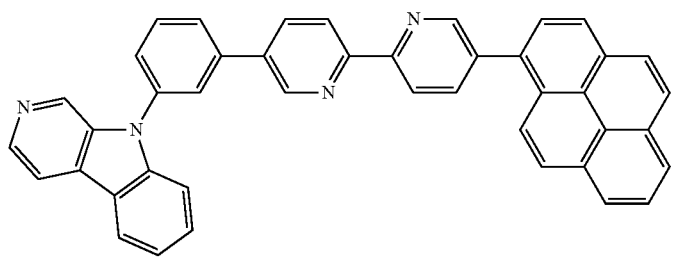
[Chem. 57]
(Compound 57)
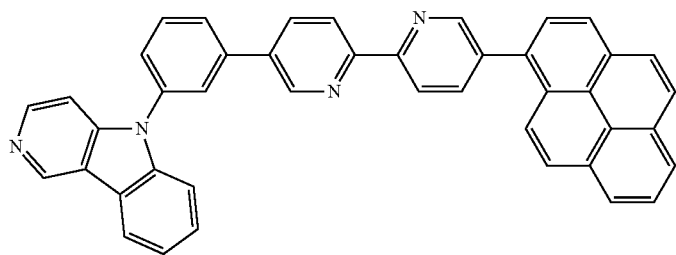
[Chem. 58]
(Compound 58)
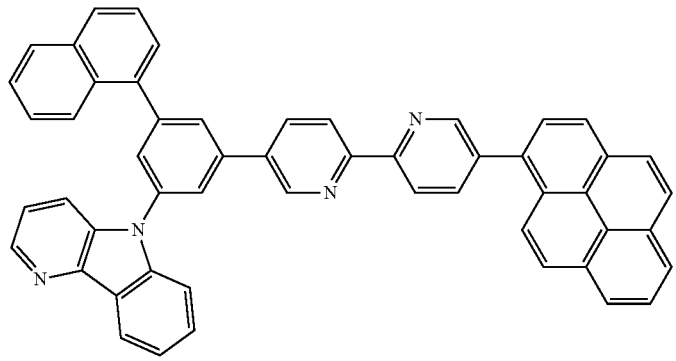

-continued
[Chem. 59]
(Compound 59)
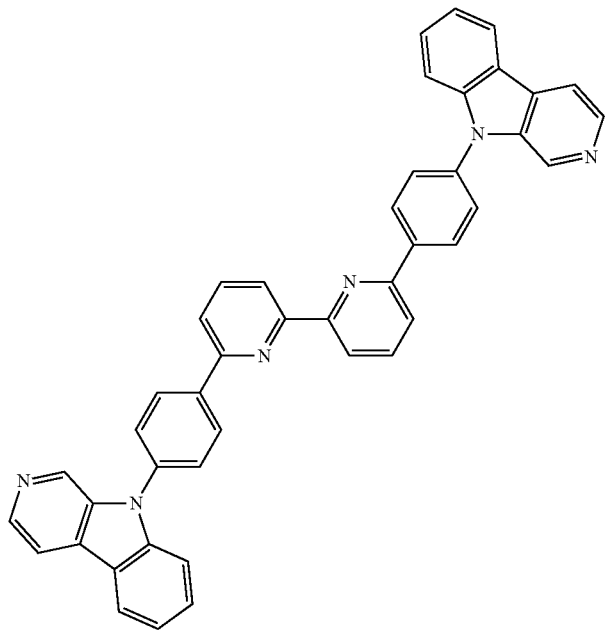
[Chem. 60]
(Compound 60)
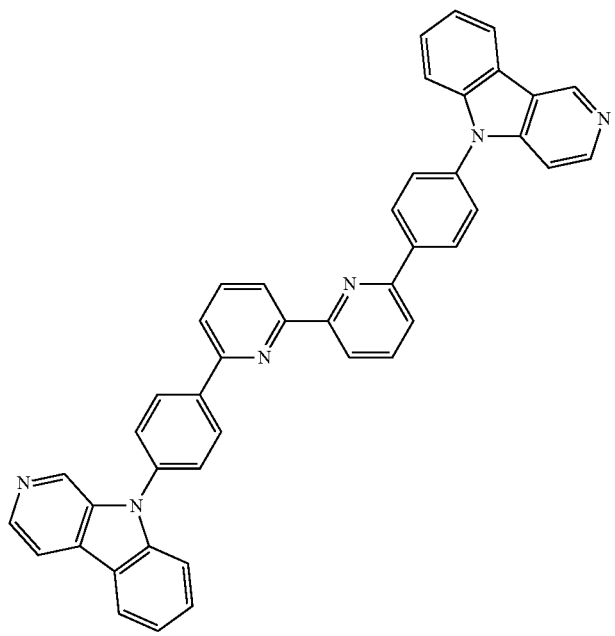

[Chem. 61]
(Compound 61)
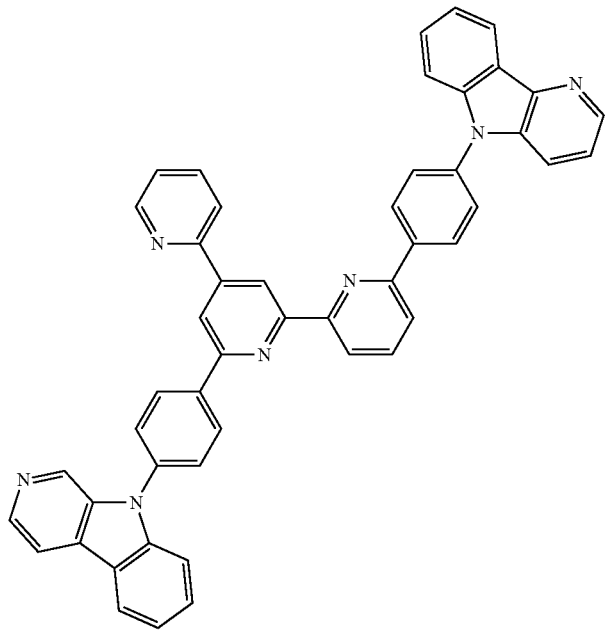
[Chem. 62]
(Compound 62)
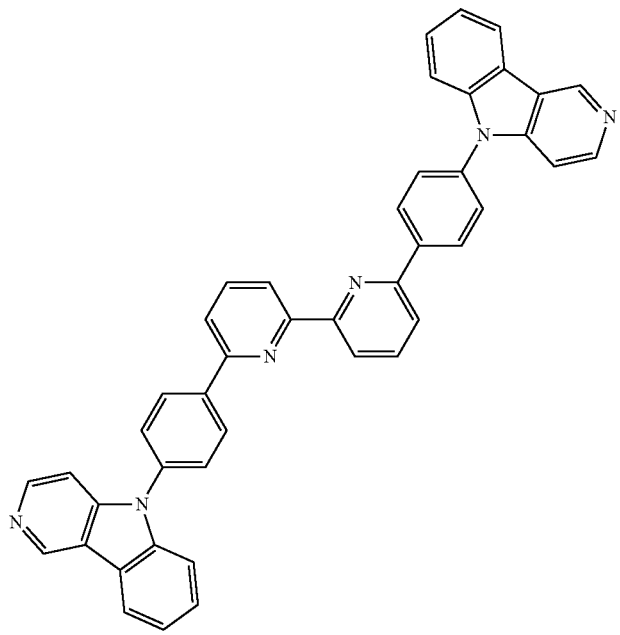

[Chem. 63]
(Compound 63)
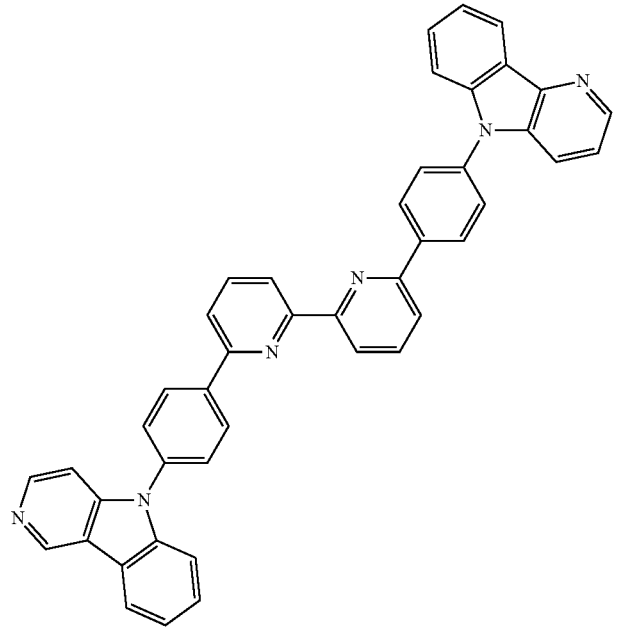
[Chem. 64]
(Compound 64)
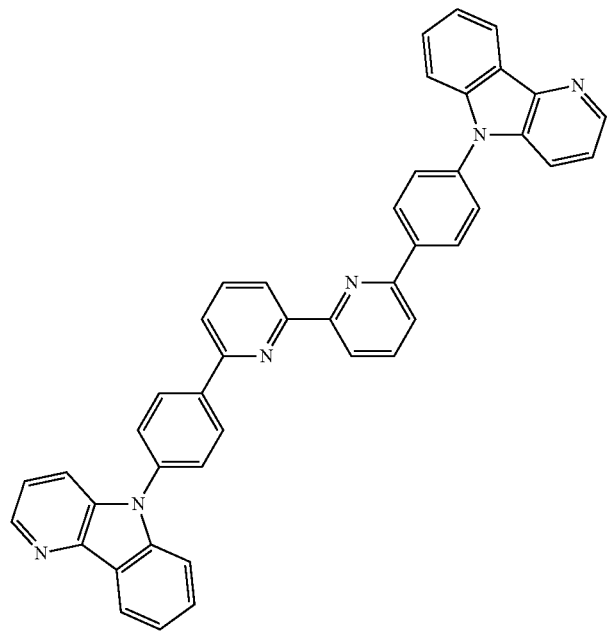

[Chem. 65]
(Compound 65)
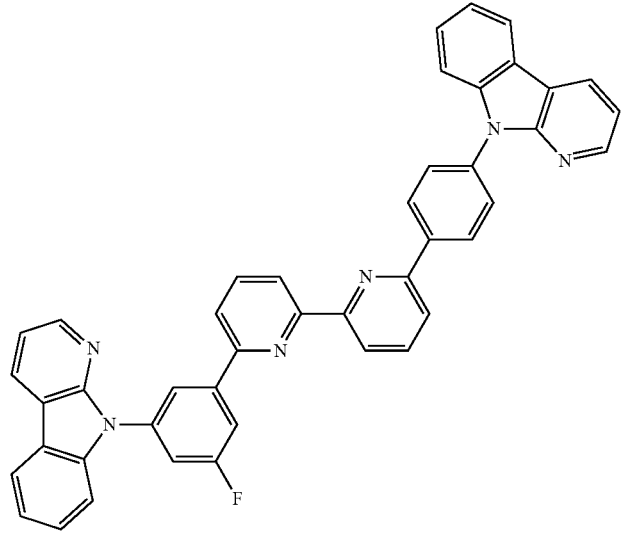
[Chem. 66]
(Compound 66)
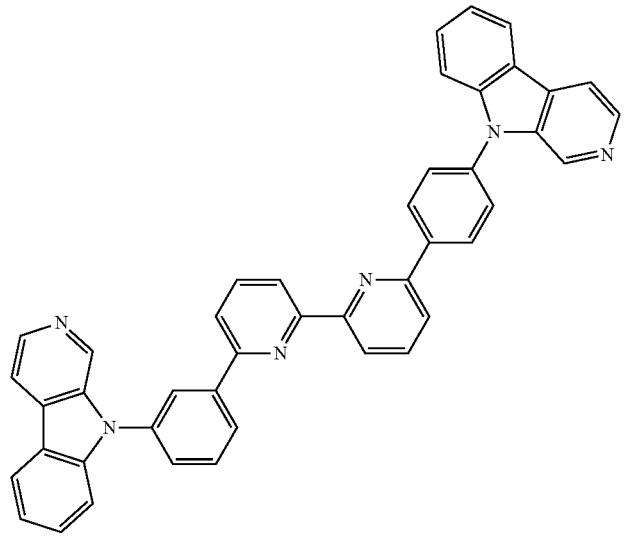

[Chem. 67]
(Compound 67)
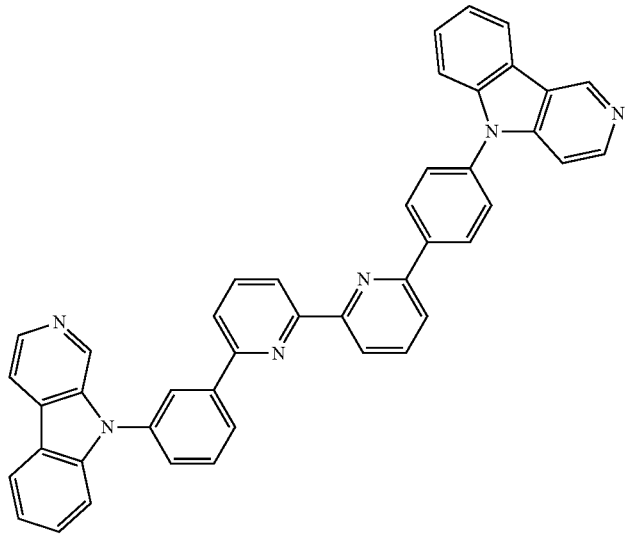
[Chem. 68]
(Compound 68)
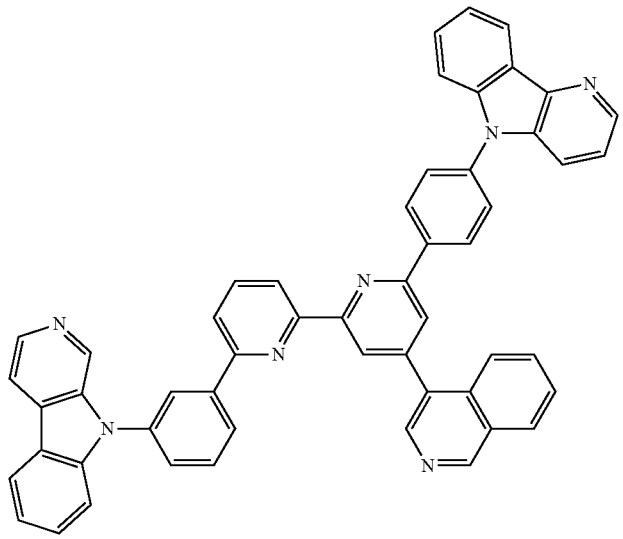

[Chem. 69]
(Compound 69)
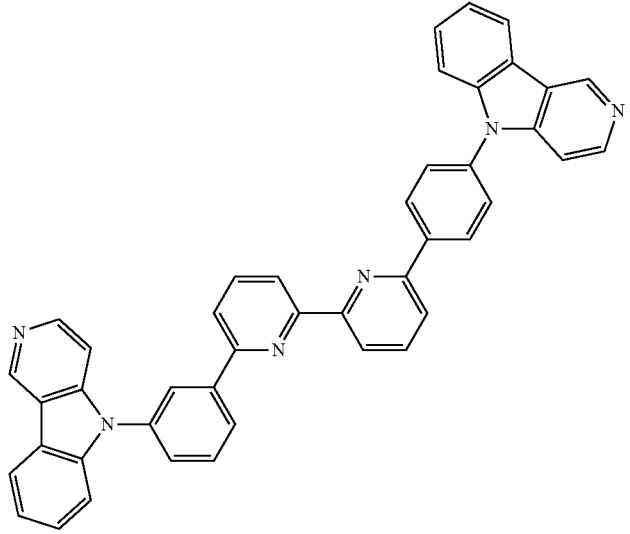
[Chem. 70]
(Compound 70)
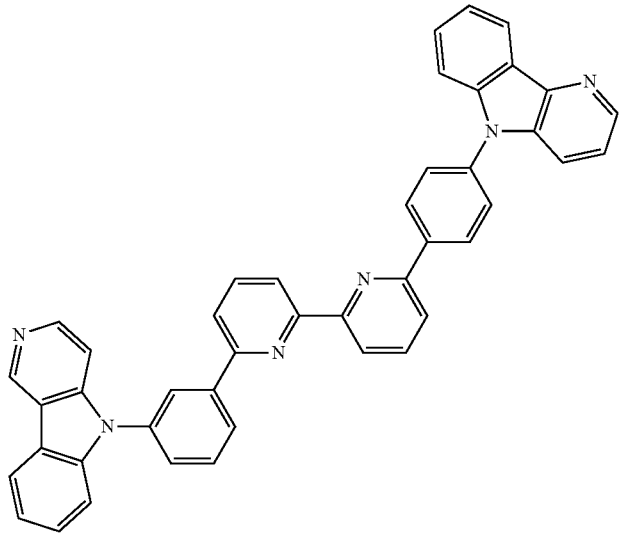

[Chem. 71]
(Compound 71)
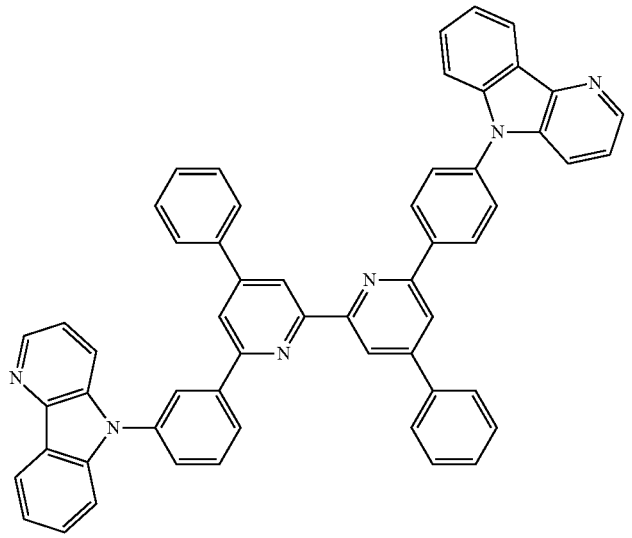
[Chem. 72]
(Compound 72)
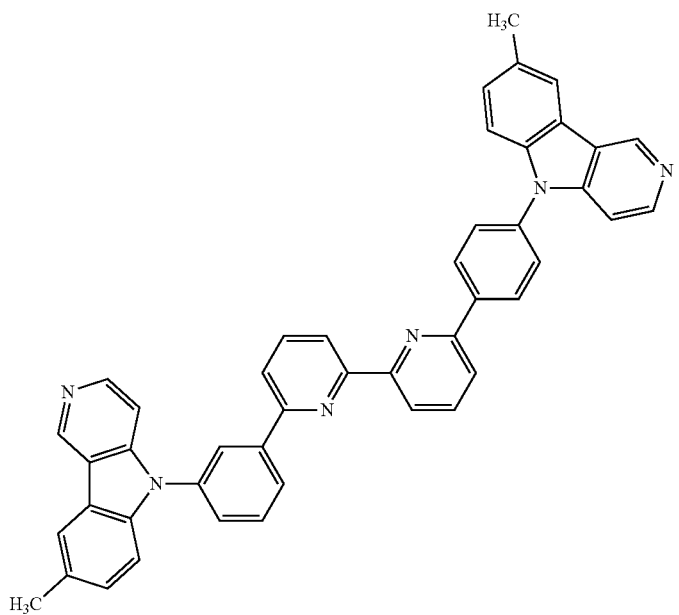

[Chem. 73]
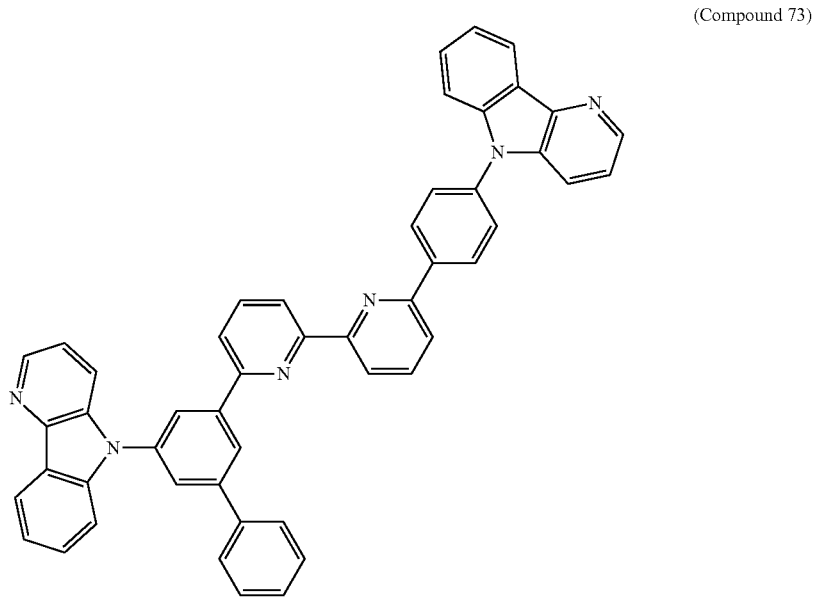
(Compound 73)
[Chem. 74]
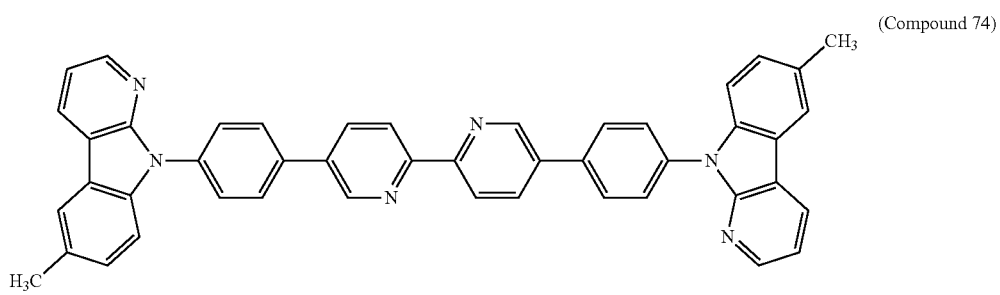
(Compound 74)
[Chem. 75]
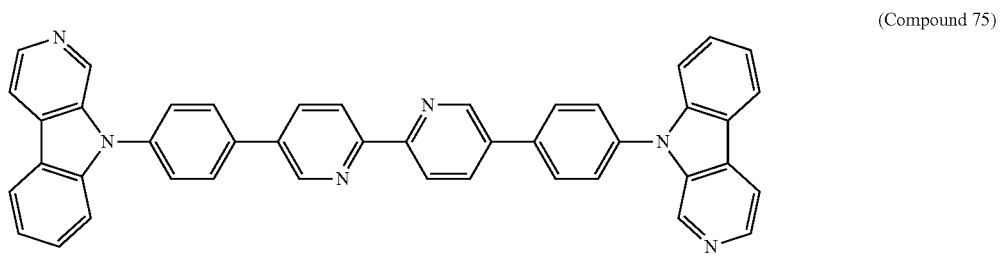
(Compound 75)
[Chem. 76]
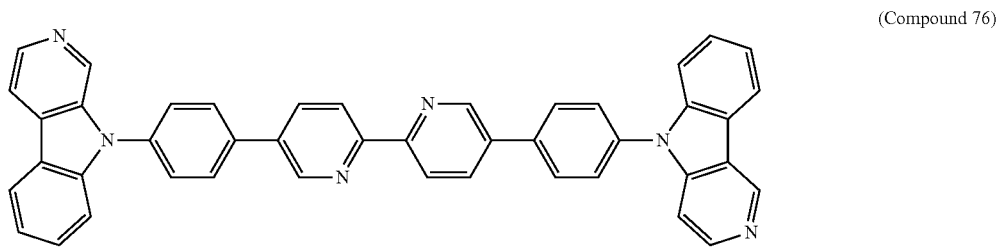
(Compound 76)

[Chem. 77]
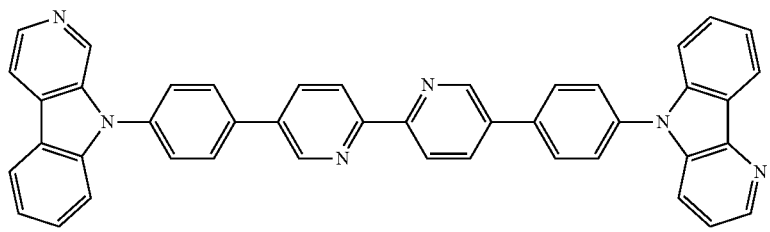
(Compound 77)
[Chem. 78]
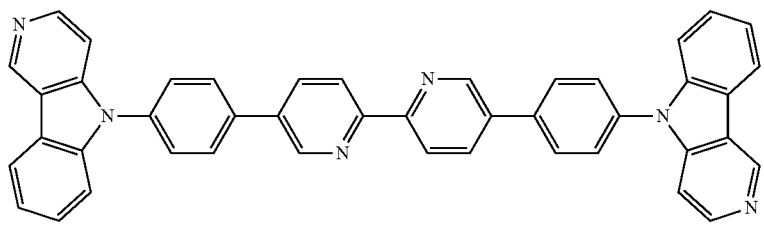
(Compound 78)
[Chem. 79]
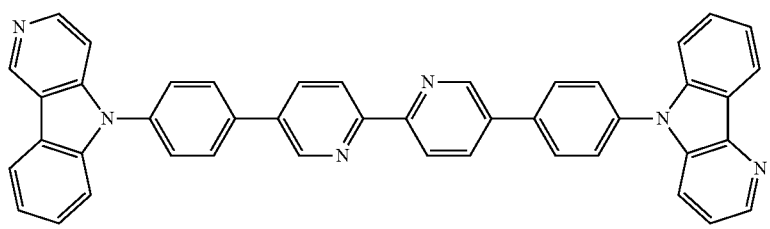
(Compound 79)
[Chem. 80]
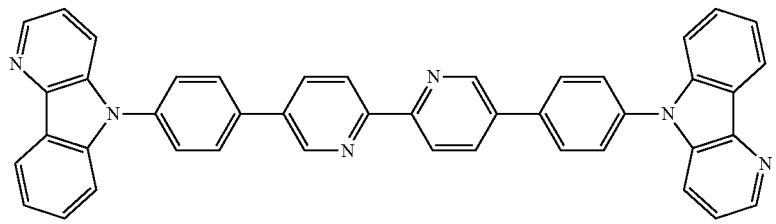
(Compound 80)
[Chem. 81]
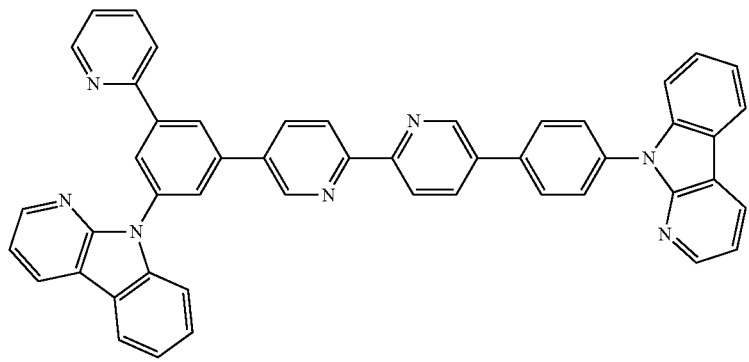
(Compound 81)

-continued
[Chem. 82]
(Compound 82)
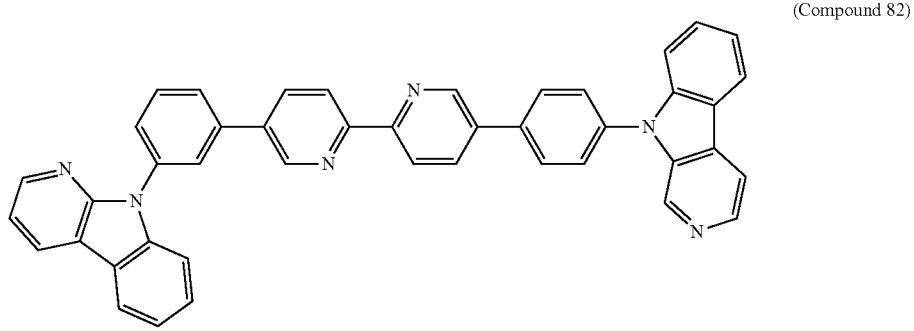
[Chem. 83]
(Compound 83)
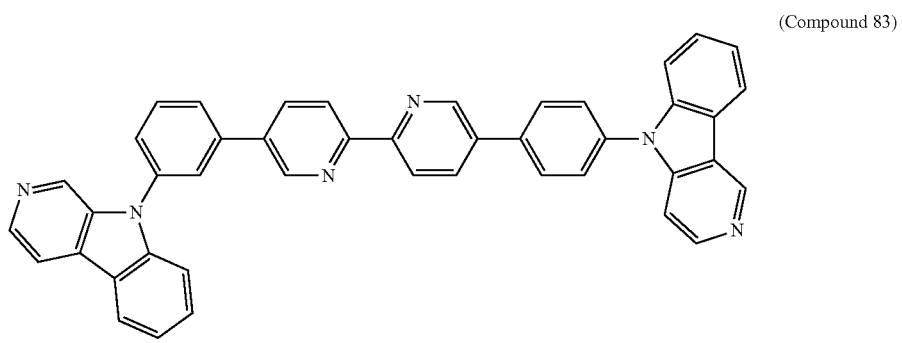
[Chem. 84]
(Compound 84)
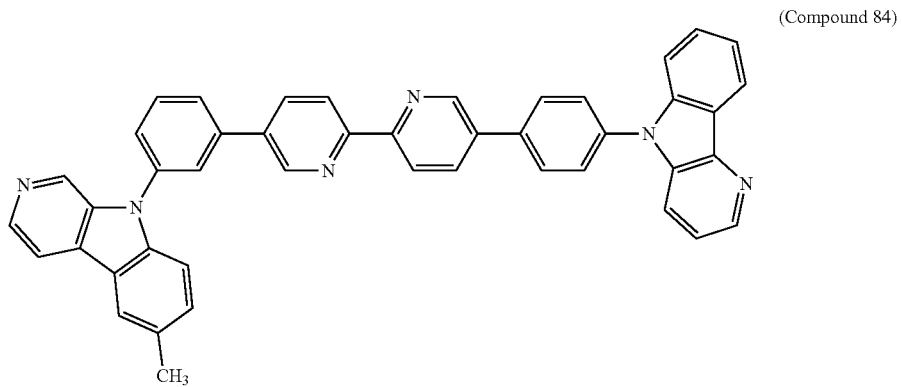
[Chem. 85]
(Compound 85)
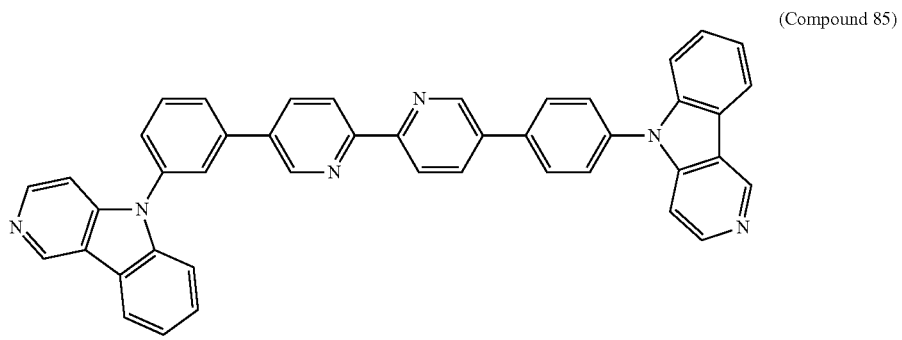

[Chem. 86]
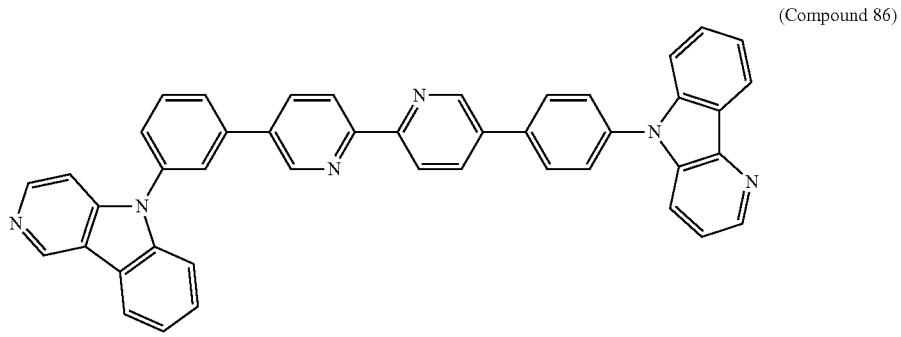
(Compound 86)
[Chem. 87]
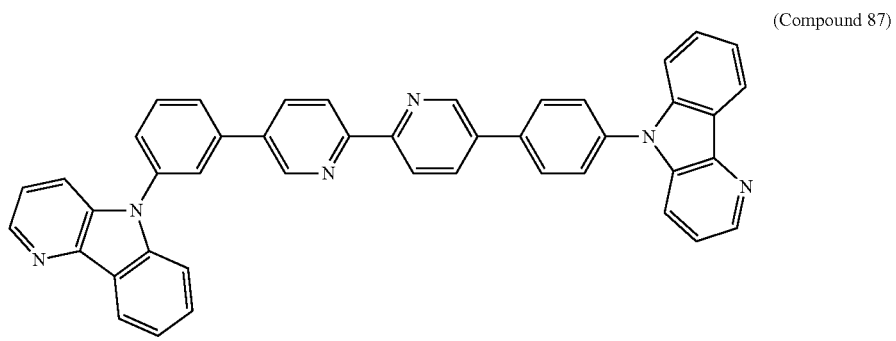
(Compound 87)
[Chem. 88]
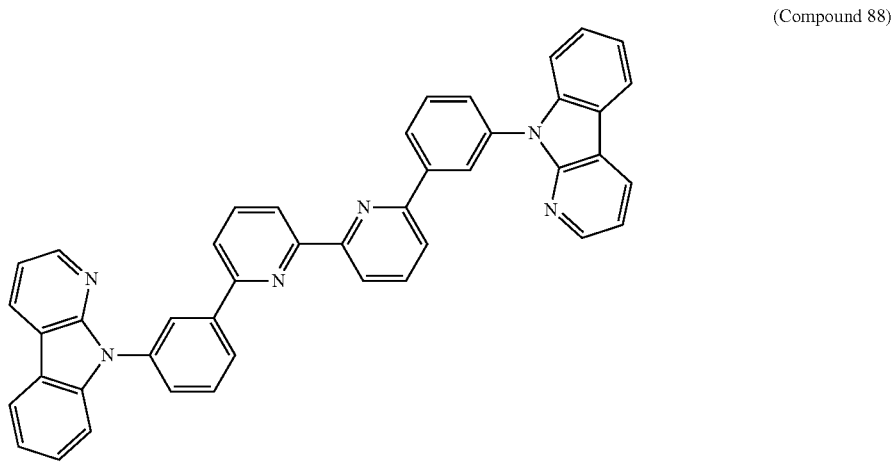
(Compound 88)

-continued
[Chem. 89]
(Compound 89)
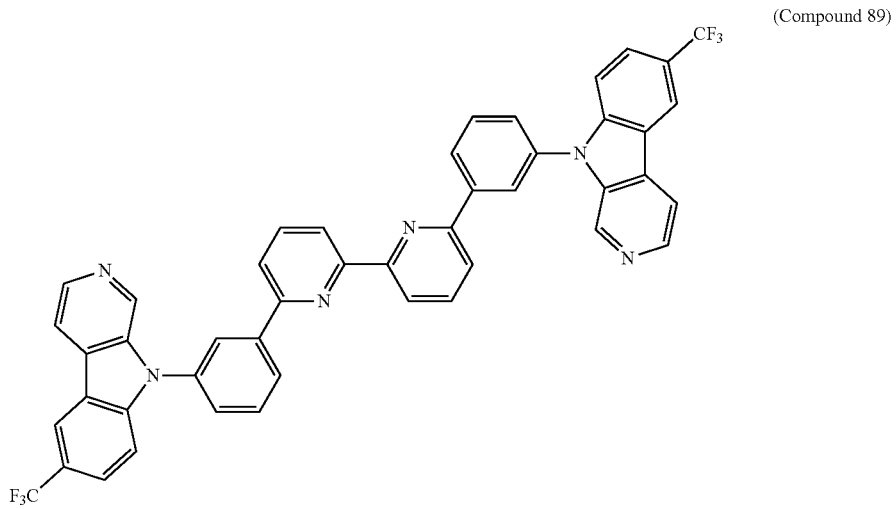
[Chem. 90]
(Compound 90)
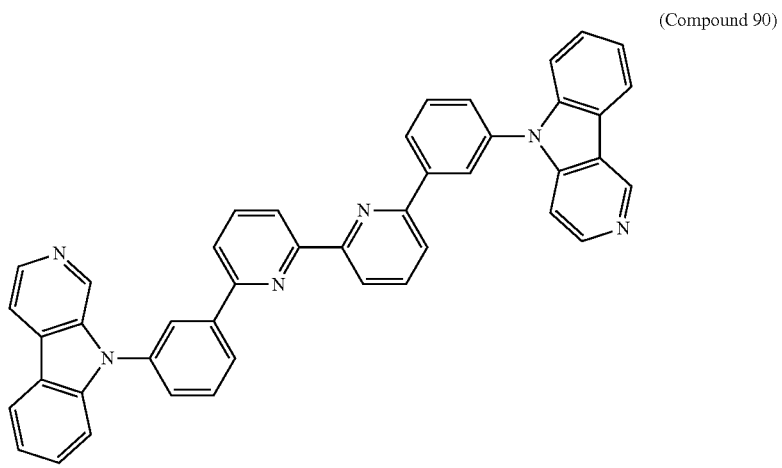
[Chem. 91]
(Compound 91)
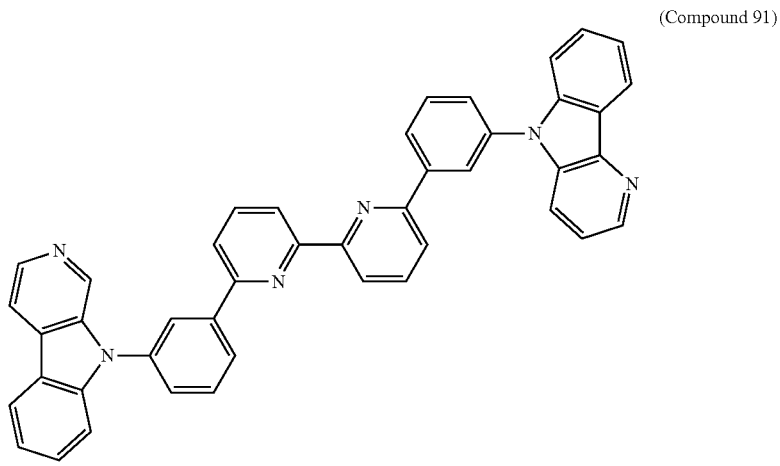

-continued
[Chem. 92]
(Compound 92)
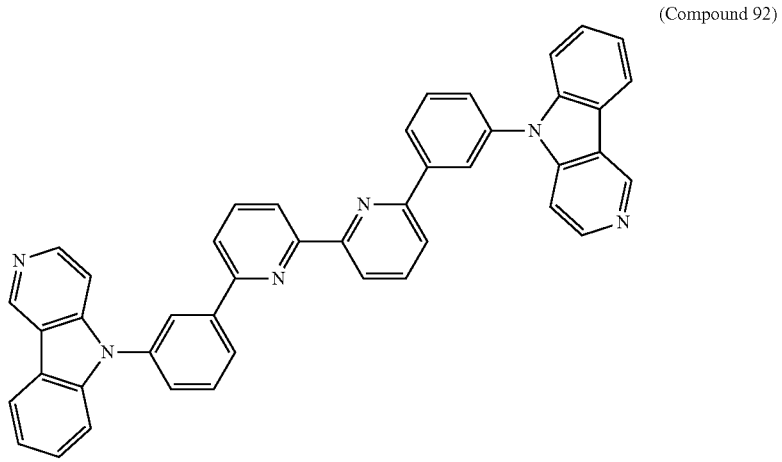
[Chem. 93]
(Compound 93)
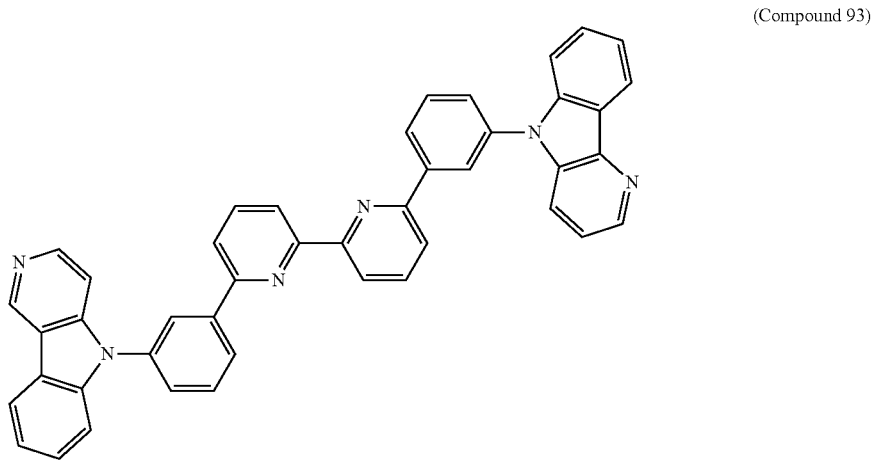
[Chem. 94]
(Compound 94)
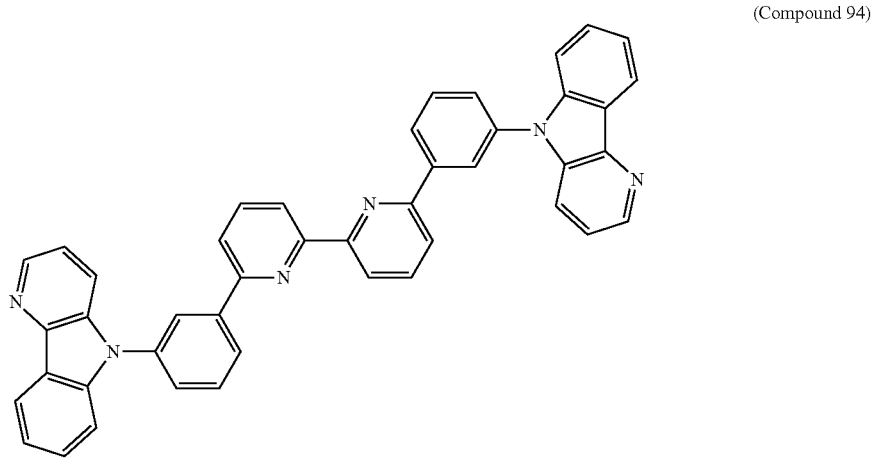

[Chem. 95]
(Compound 95)
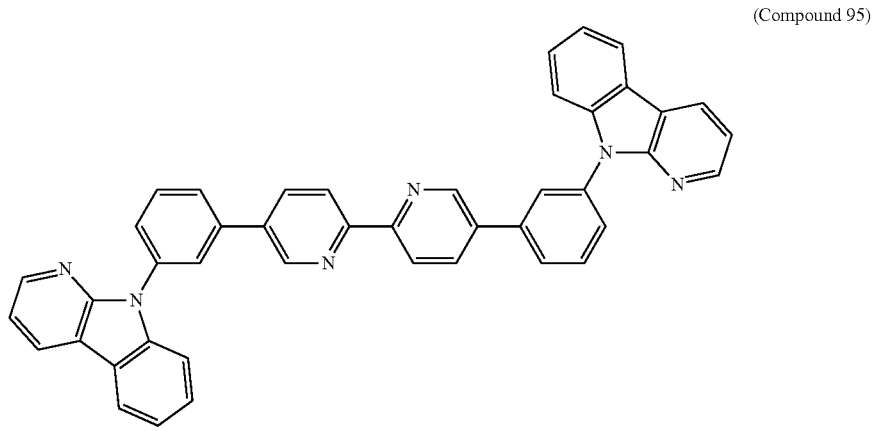
[Chem. 96]
(Compound 96)
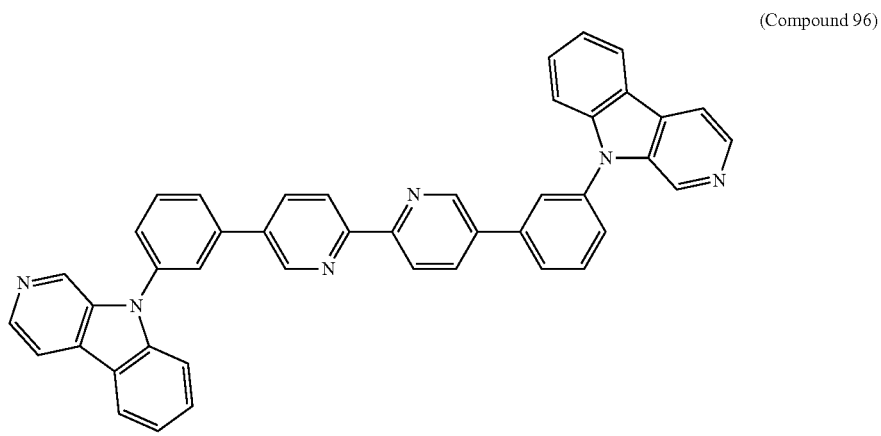
[Chem. 97]
(Compound 97)
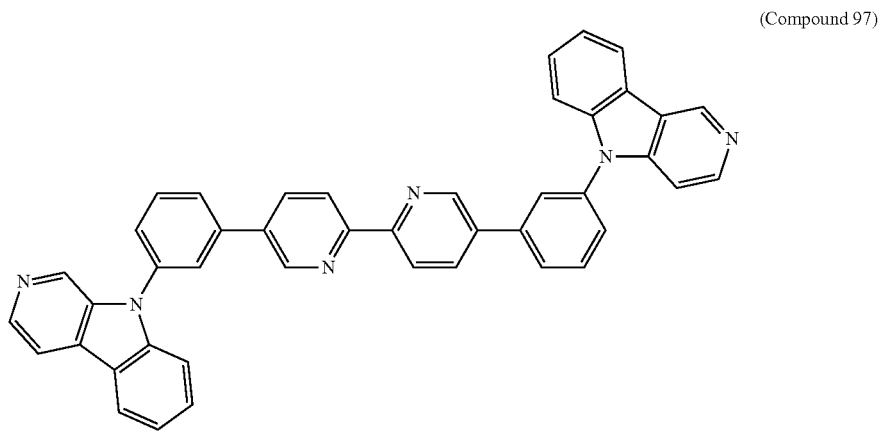

[Chem. 98]
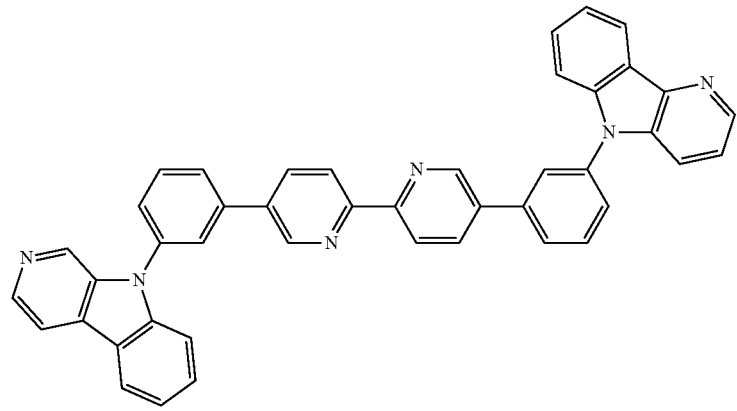
(Compound 98)
[Chem. 99]
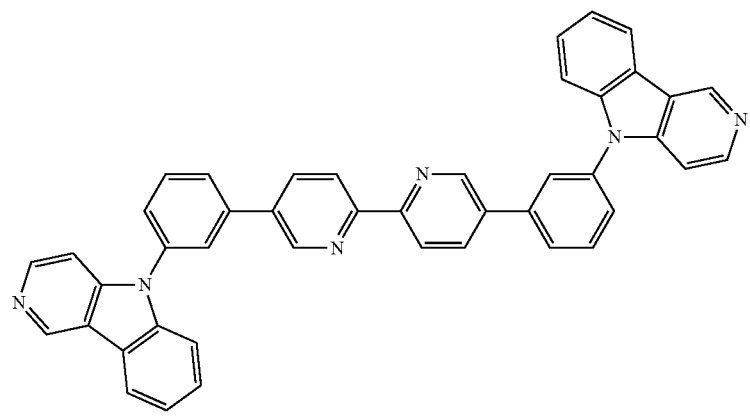
(Compound 99)
[Chem. 100]
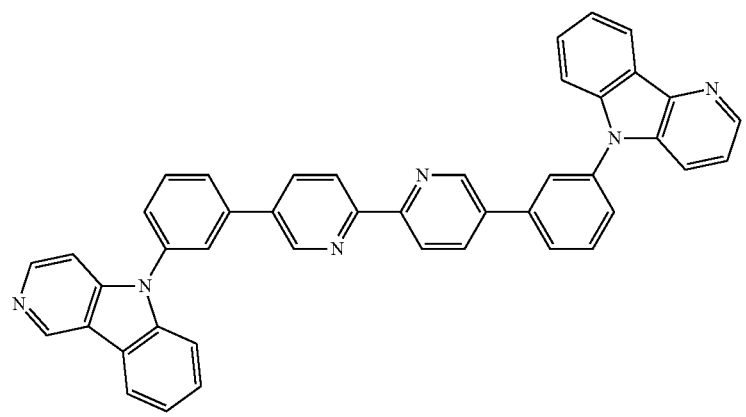
(Compound 100)

[Chem. 101]
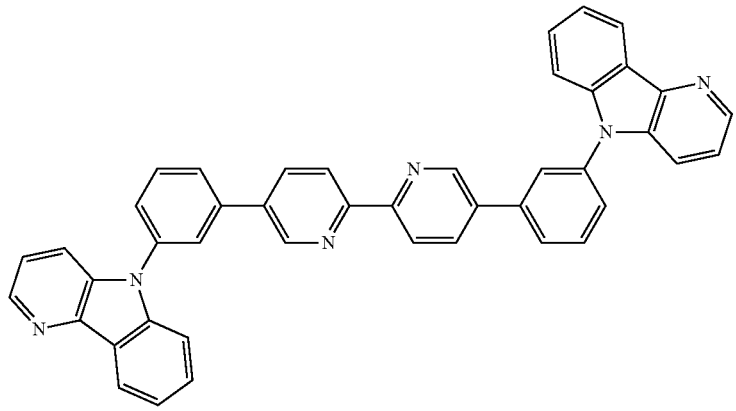
(Compound 101)
[Chem. 102]
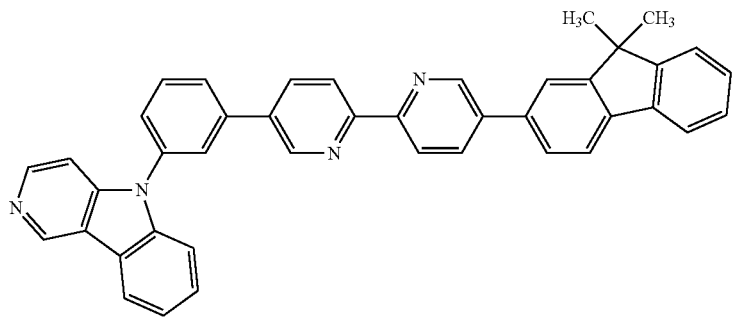
(Compound 102)
[Chem. 103]
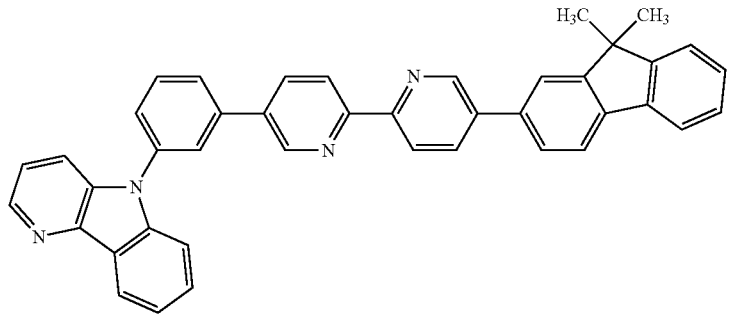
(Compound 103)

[Chem. 104]
(Compound 104)
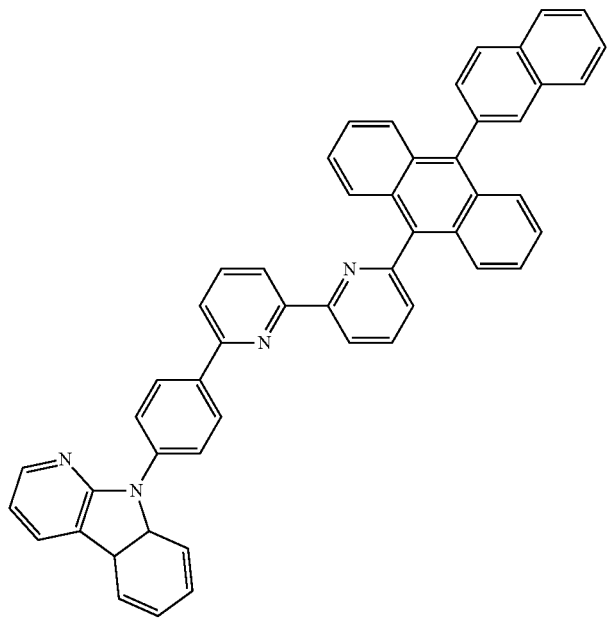
[Chem. 105]
(Compound 105)
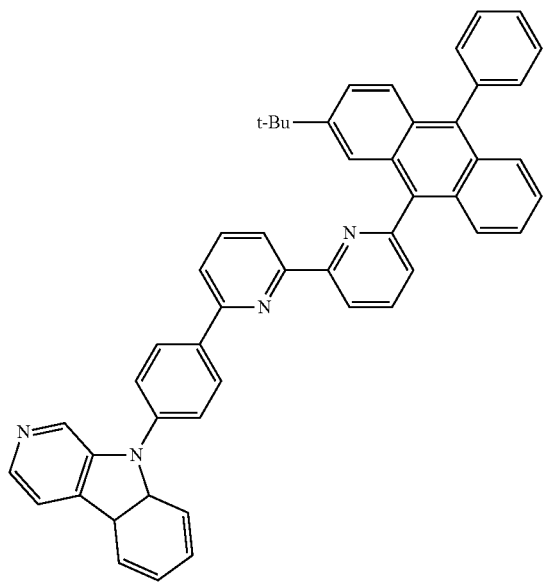

[Chem. 106]
(Compound 106)
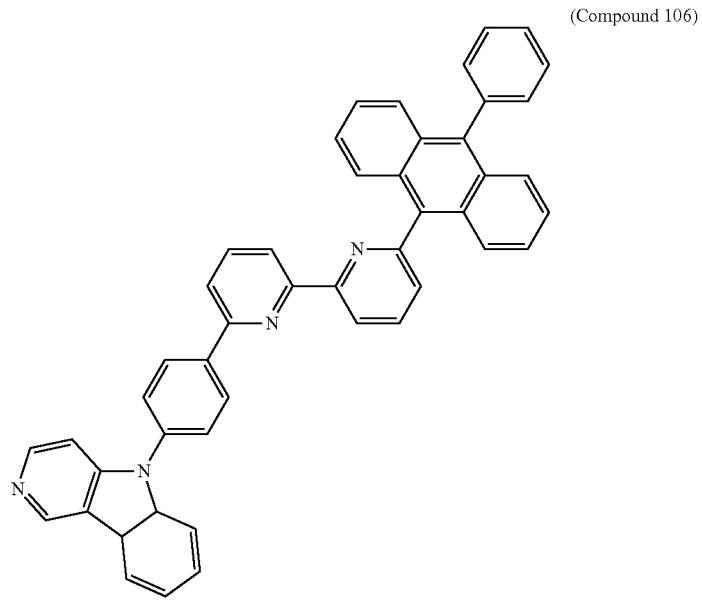
[Chem. 107]
(Compound 107)
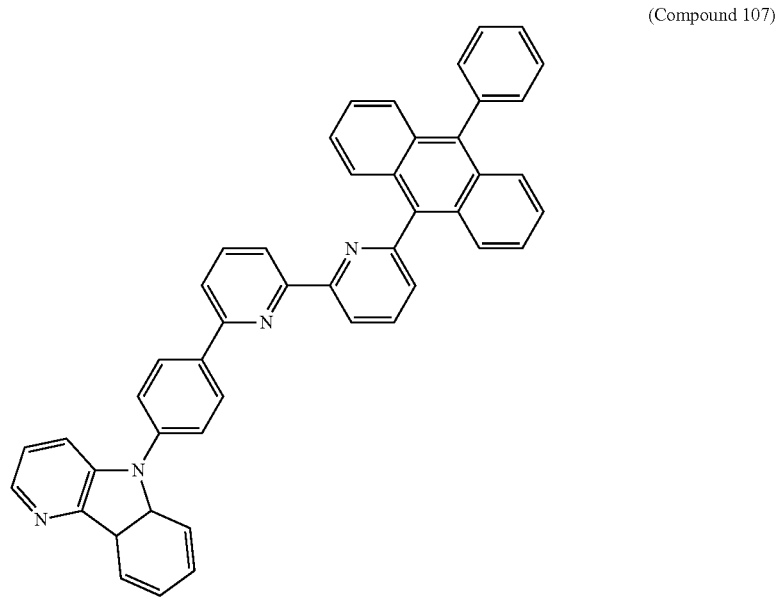

-continued
[Chem. 108]
(Compound 108)
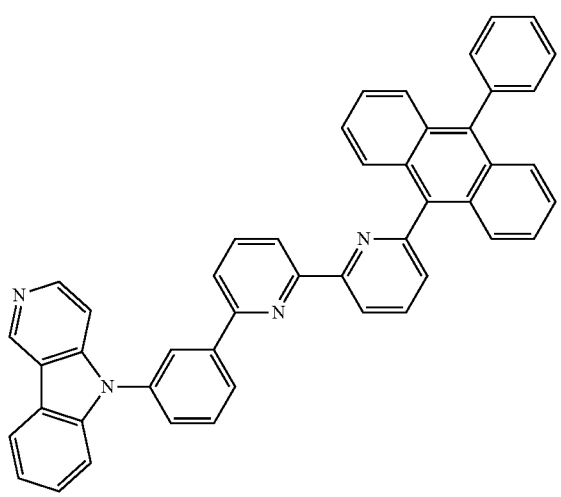
[Chem. 109]
(Compound 109)
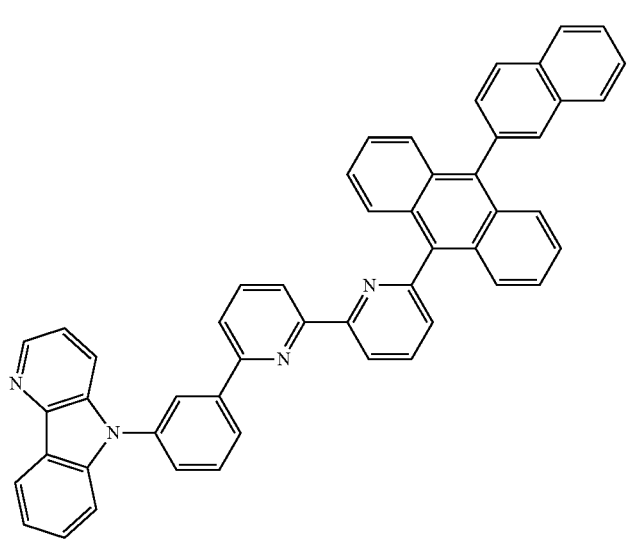
[Chem. 110]
(Compound 110)
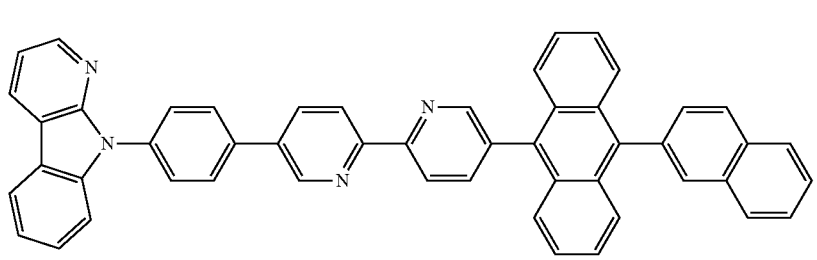
[Chem. 111]
(Compound 111)
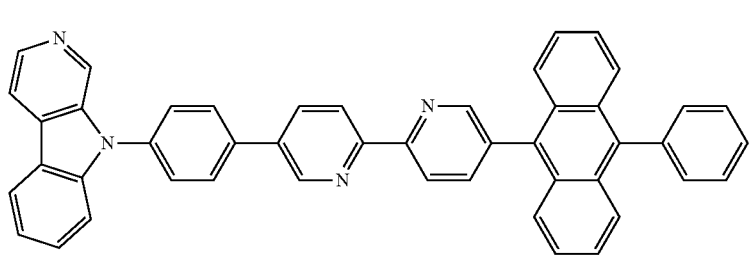

[Chem. 112]
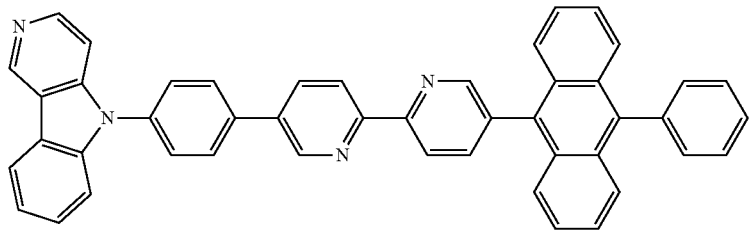
(Compound 112)
[Chem. 113]
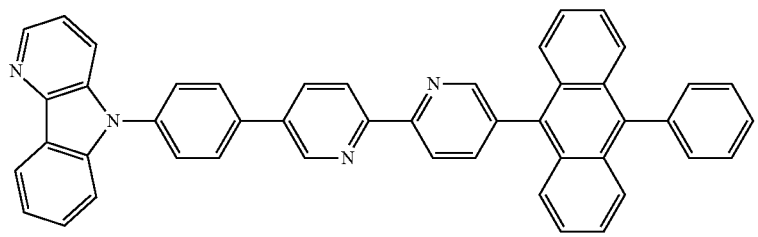
(Compound 113)
[Chem. 114]
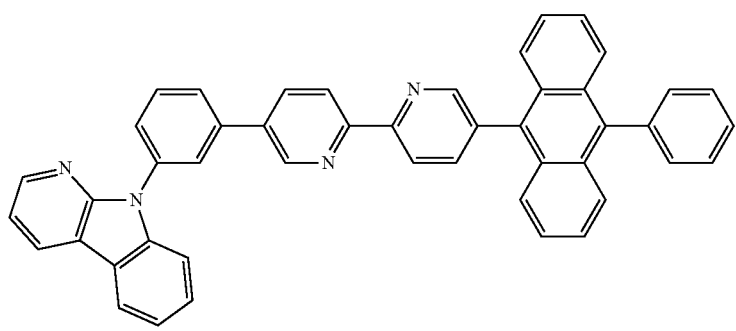
(Compound 114)
[Chem. 115]
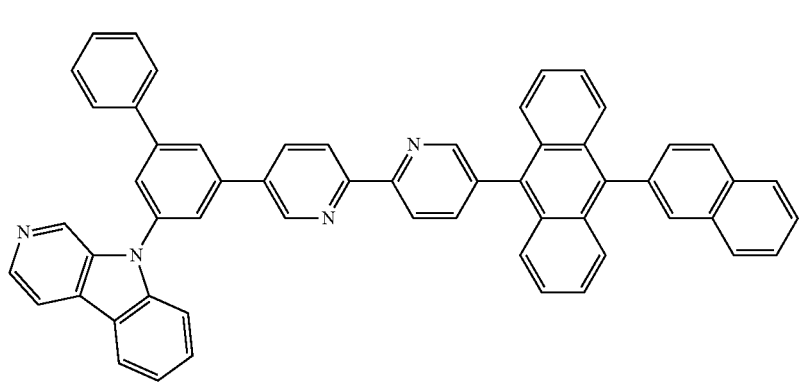
(Compound 115)

[Chem. 116]
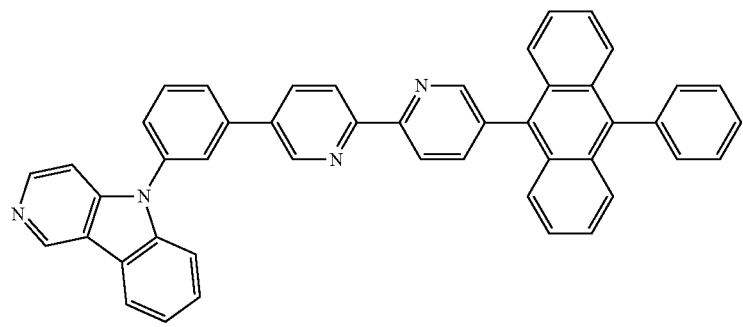
(Compound 116)
[Chem. 117]
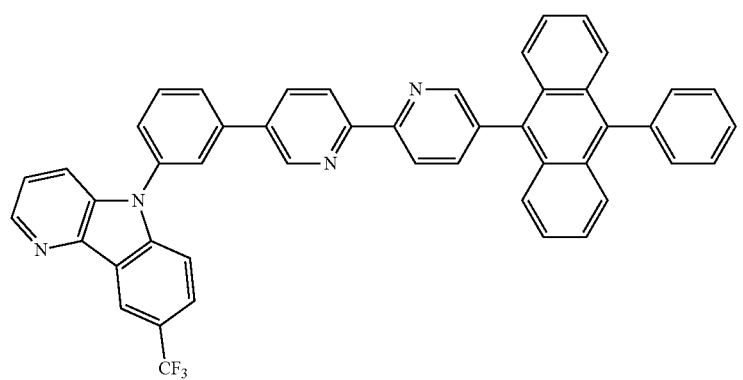
(Compound 117)
[Chem. 118]
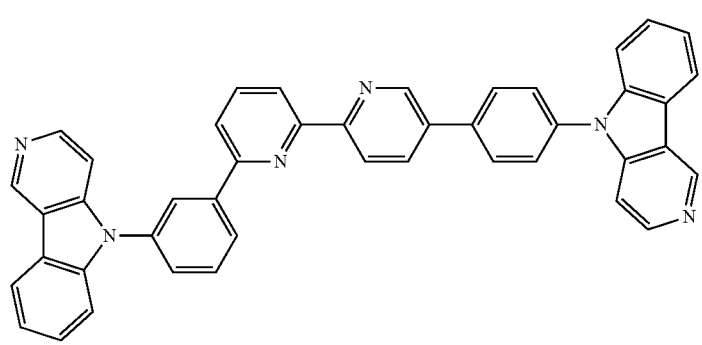
(Compound 118)

-continued
[Chem. 119]
(Compound 119)
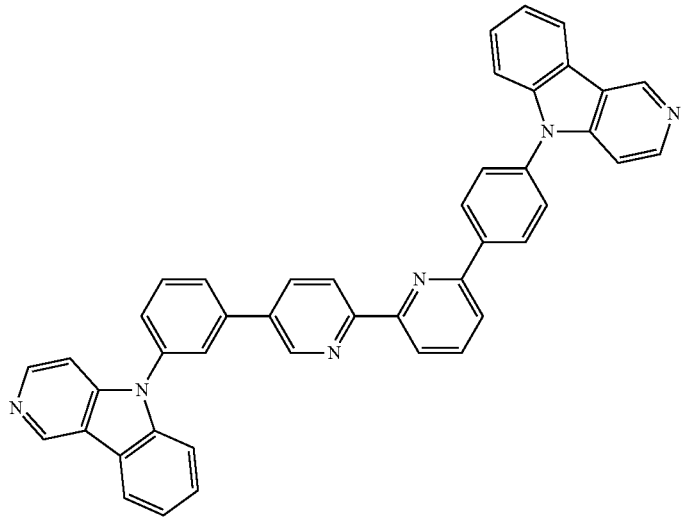
[Chem. 120]
(Compound 120)
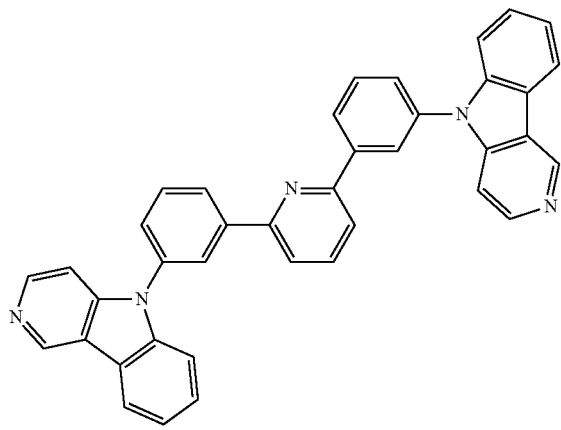
[Chem. 121]
(Compound 121)
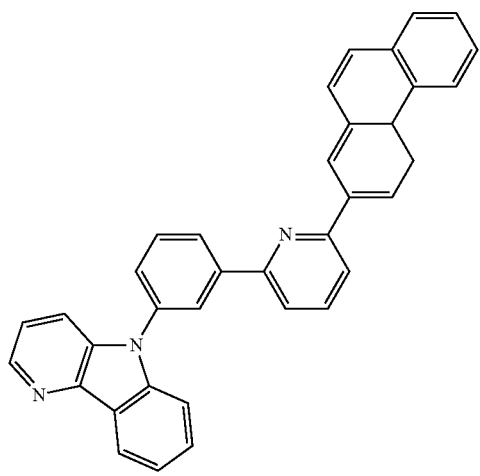

[Chem. 122]
(Compound 122)
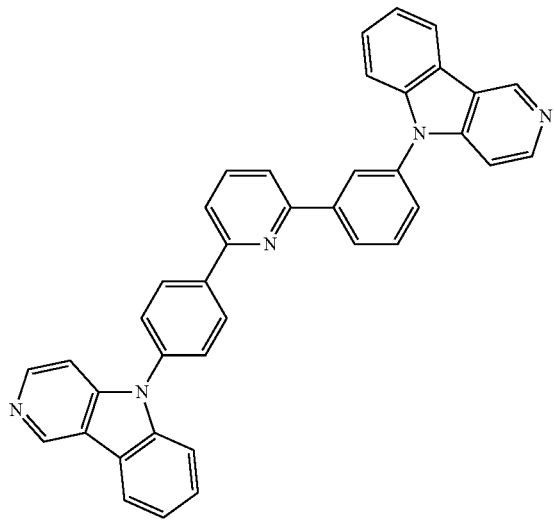
[Chem. 123]
(Compound 123)
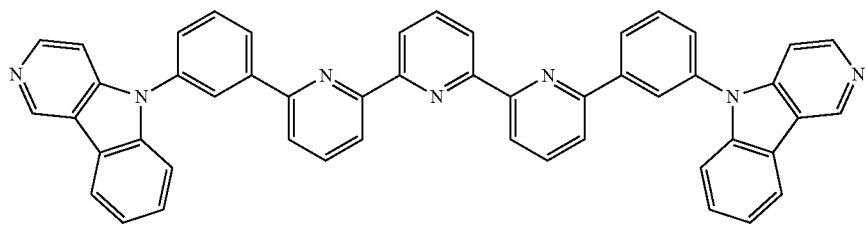
[Chem. 124]
(Compound 124)
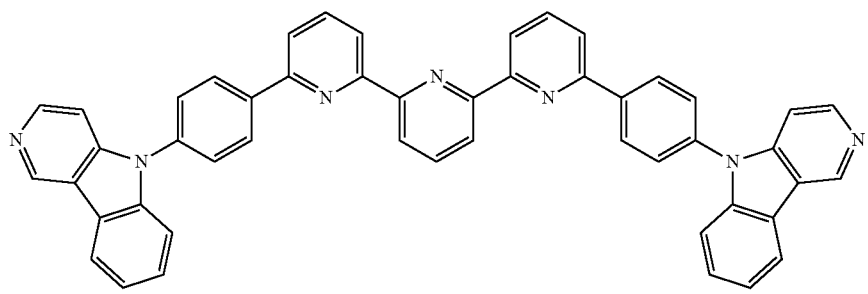

[Chem. 125]
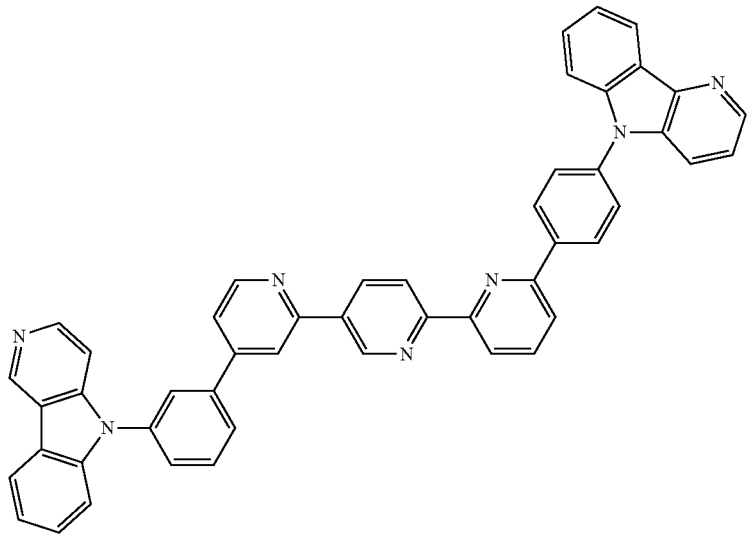
(Compound 125)
[Chem. 126]
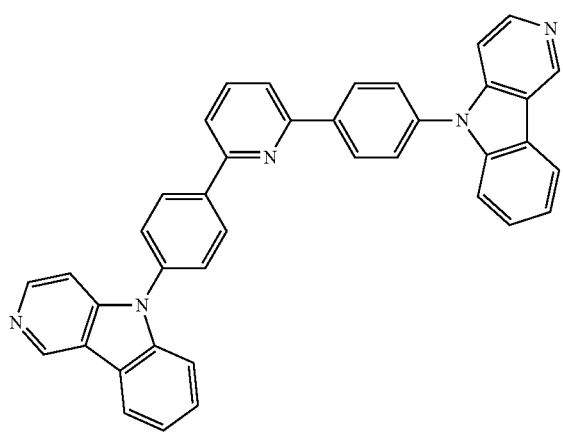
(Compound 126)
[Chem. 127]
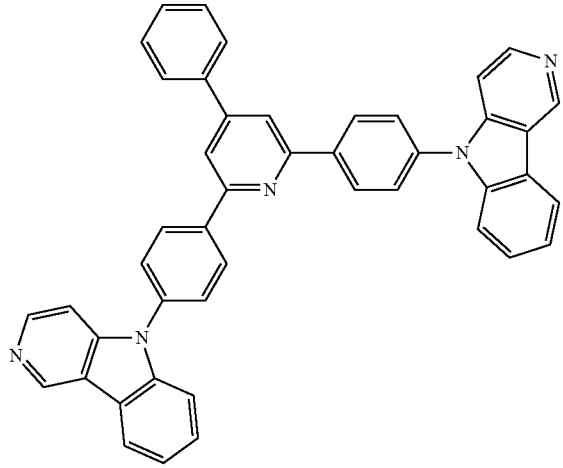
(Compound 127)

[Chem. 128]

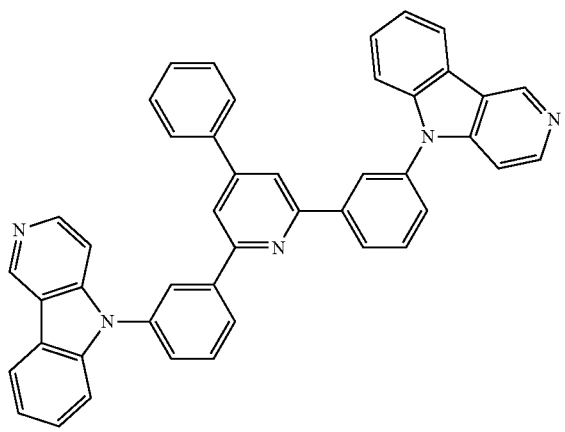

(Compound 128)

Purification of these compounds was performed by purification by column chromatography, adsorption purification with active carbon, activated clay, or the like, a recrystallization or crystallization method with a solvent, or the like. Identification of the compounds was performed by NMR analysis. As physical properties, DSC measurement (Tg) and melting point measurement were carried out. The melting point serves as an indicator of vapor deposition properties and the glass transition point (Tg) serves as an indicator of stability in a thin-film state.

The melting point and the glass transition point were measured using a powder material by means of a highly sensitive differential scanning calorimeter DSC 3100S manufactured by Bruker AXS.

Further, the work function was measured by preparing a thin film of 100 nm on an ITO substrate and using a photoelectron spectroscopy in air (Model AC-3, manufactured by Riken Keiki Co., Ltd.). The work function is regarded as an indicator of hole-blocking ability.

Examples of the structure of the organic EL device of the invention include a structure having an anode, a hole-injecting layer, a hole-transporting layer, an emitting layer, a hole-blocking layer, an electron-transporting layer and a cathode in this order on a substrate, and a structure further having an electron-injecting layer between the electron-transporting layer and the cathode. In these multilayer structures, it is possible to omit several layers of the organic layers and, for example, the structure may have a constitution sequentially having an anode, a hole-transporting layer, an emitting layer, an electron-transporting layer and a cathode on a substrate.

As the anode of the organic EL device, an electrode material having a large work function, such as ITO or gold, is used. As the hole-injecting layer, besides copper phthalocyanine (hereinafter referred to as CuPc), materials such as star-burst type triphenylamine derivatives and wet-process type materials may be employed.

For the hole-transporting layer, there may be used N,N'-diphenyl-N,N'-di(m-tolyl)-benzidine (hereinafter referred to as TPD) and N,N'-diphenyl-N,N'-di(α-naphthyl)-benzidne (hereinafter referred to as NPD), which are one of benzidne derivatives, various triphenylamine tetramers, and the like. Further, as the hole-injecting/transporting layers, wet-process type polymer materials such as PEDOT/PSS may be employed.

As the emitting layer, hole-blocking layer, and electron-transporting layer of the organic EL device of the invention, besides the compound having a substituted pyridyl group and a pyridoindole ring structure linked through a phenylene group, aluminum complexes, thiazole derivatives, oxazole derivatives, carbazole derivatives, polydialkylfluorene derivatives, and the like may be used.

By using a conventional luminescence material such as an aluminum complex or styryl derivative for the emitting layer and using the compound having a substituted pyridyl group and a pyridoindole ring structure linked through a phenylene group as the hole-blocking layer and the electron-transporting layer, a high-performance organic EL device can be prepared. Further, a high-performance organic EL device can be prepared also by adding a dopant, for example, a fluorescent material such as quinacridone, coumarin or rubrene or a phosphorescent material such as an iridium complex of phenylpyridine, as a host material of the emitting layer.

Furthermore, the compound having a substituted pyridyl group and a pyridoindole ring structure linked through a phenylene group can be used as the electron-transporting layer through multilayering or co-deposition with conventional electron-transporting material(s).

The organic EL device of the invention may have an electron-injecting layer. As the electron-injecting layer, lithium fluoride or the like may be used. For the cathode, an electrode material having a low work function such as aluminum, or an alloy having a low work function such as aluminum magnesium is used as an electrode material.

Embodiments of the invention will be illustrated in greater detail with reference to the following Examples, but the invention should not be construed as being limited thereto so long as not exceeding the gist of the invention.

EXAMPLE 1

(Synthesis of 5,5'-bis[3-(5H-pyrido[4,3-b]indol-5-yl)phenyl]-[2,2']bipyridine (Compound 99))

A reaction vessel was charged with 6.0 g of 2,5-dibromopyridine, 7.0 ml of bistributyltin, and 120 ml of xylene, followed by heating and stirring at 60° C. for 15 minutes. Further, 700 mg of tetrakis(triphenylphosphine)palladium was added thereto, followed by stirring at 120° C. for 8 hours. After cooling to room temperature, the insoluble materials were removed by filtration, and the filtrate was washed with 150 ml of an aqueous ethylenediamine tetraacetate solution. The organic layer was dehydrated with anhydrous sodium sulfate and concentrated under reduced pressure to obtain a crude product. The crude product was purified by column chromatography (carrier: silica gel, eluent: cyclohexane/toluene) to obtain 1.7 g (yield 42%) of 5,5'-dibromo-[2,2']bipyridine as a yellow powder.

Another reaction vessel was charged with 17.2 ml of 1,3-dibromobenzene, 6.0 g of 5H-pyrido[4,3-b]indole, 1.1 g of copper powder, 9.9 g of potassium carbonate, and 0.6 ml of dimethyl sulfoxide, followed by heating and stirring at 180° C. for 4 hours. After cooling to room temperature, 50 ml of chloroform was added thereto, the insoluble materials were removed by filtration and the filtrate was concentrated under reduced pressure to obtain a crude product. The crude product was purified by column chromatography (carrier: silica gel, eluent: hexane/chloroform) to obtain 7.1 g (yield 62%) of 5-(3-bromophenyl)-5H-pyrido[4,3-b]indole as a white powder.

To 7.1 g of the resulting 5-(3-bromophenyl)-5H-pyrido[4,3-b]indole were added 6.7 g of bis(pinacolato)diboron, 6.7 g of potassium acetate, 540 mg of bis(diphenylphosphinoferrocene)dipalladium, and 100 ml of dimethyl sulfoxide, followed by heating and stirring at 80° C. for 5 hours. After cooling to room temperature, 200 ml of ethyl acetate and 100 ml of water were added thereto to separate the liquid, and the aqueous layer was further extracted with 100 ml of ethyl acetate. The organic layer was combined, dehydrated with anhydrous magnesium sulfate, and then concentrated under reduced pressure to obtain a crude product. The crude product was purified by column chromatography (carrier: NH silica gel, eluent: chloroform) to obtain 4.4 g (yield 53%) of 5-[3-(4,4,5,5-tetramethyl-[1,3,2]dioxaborolan-2-yl)phenyl]-5H-pyrido[4,3-b]indole as a yellow powder.

To 2.8 g of the resulting 5-[3-(4,4,5,5-tetramethyl-[1,3,2]dioxaborolan-2-yl)phenyl]-5H-pyrido[4,3-b]indole were added 1.2 g of 5,5'-dibromo[2,2']bipyridine that had been synthesized in advance, 440 mg of tetrakis(triphenylphosphine)palladium, 9.4 ml of a 2 M aqueous potassium carbonate solution, 32 ml of toluene, and 8 ml of ethanol, followed by heating with reflux while stirring for 8 hours. After cooling to room temperature, the precipitate was separated by filtration. The precipitate was dissolved in a mixed solvent of chloroform/methanol, the insoluble materials were removed by filtration and the filtrate was concentrated under reduced pressure to obtain a crude product. The crude product was purified by column chromatography (carrier: NH silica gel, eluent: chloroform) to obtain 1.7 g (yield 71%) of 5,5'-bis[3-(5H-pyrido[4,3-b]indol-5-yl]phenyl]-[2,2]bipyridine (Compound 99) as a yellowish white powder.

The structure of the resulting yellowish white powder was identified using NMR. The results of 1H-NMR measurement are shown in FIG. 1.

The following 28 hydrogen signals were detected on 1H-NMR (CDCl3). δ (ppm)=9.42(2H), 9.01 (2 H), 8.57(4 H), 8.25(2 H), 8.11(2 H), 7.78-7.86(6 H), 7.63(2 H), 7.52(4 H), 7.42(2 H), 7.38(2 H).

EXAMPLE 2

(Synthesis of 2,6-bis[4-(5H-pyrido[4,3-b]indol-5-yl) phenyl]pyridine (Compound 126))

As in Example 1, 5-(4-bromophenyl)-5H-pyrido[4,3-b]indole was synthesized from 1,4-dibromobenzene and 5H-pyrido[4,3-b]indole, and further subjected to a reaction with bis(pinacolato)diborone to synthesize 5-[4-(4,4,5,5-tetramethyl-[1,3,2]dioxaborolan-2-yl)phenyl]-5H-pyrido[4,3-b]indole. To 5.0 g of the resulting 5-[4-(4,4,5,5-tetramethyl-[1,3,2]dioxaborolan-2-yl])phenyl]-5H-pyrido[4,3-b]indole were added 1.6 g of 2,6-dibromopyridine, 0.39 g of tetrakis(triphenyl phosphine)palladium, 16.9 ml of a 2 M aqueous potassium carbonate solution, 56 ml of toluene, and 14 ml of ethanol, followed by heating with reflux while stirring for 8.5 hours. After cooling to room temperature, 50 ml of toluene and 100 ml of water were added thereto to separate the liquid and collect the organic layer. Further, the aqueous layer was extracted with 70 ml of toluene. The organic layers were combined, dehydrated with anhydrous magnesium sulfate, and then concentrated under reduced pressure to obtain a crude product. The crude product was purified by column chromatography (carrier: NH silica gel, eluent: toluene) to obtain 2.3 g (yield 60%) of 2,6-bis[4-(5H-pyrido[4,3-b]indol-5-yl)phenyl]pyridine (Compound 126) as a white powder.

Figure 2:
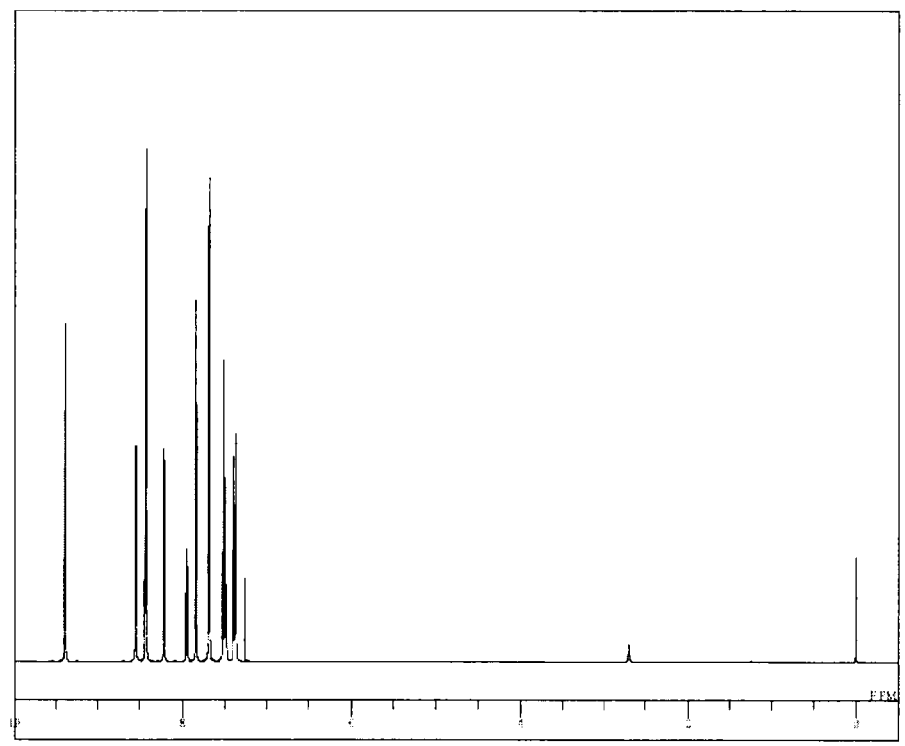
FIG. 2 is a 1H-NMR chart of the compound (Compound 126) of Invention Example 2.

The structure of the resulting white powder was identified using NMR. The results of 1H-NMR measurement are shown in FIG. 2.

The following 25 hydrogen signals were detected on 1H-NMR (CDCl3). δ (ppm)=9.40(2H), 8.55 (2 H), 8.43(4 H), 8.22(2 H), 7.95(1 H), 7.84(2 H), 7.69(4 H), 7.46-7.54(4 H), 7.34-7.41(4 H).

EXAMPLE 3

For the compounds of the invention, melting point and glass transition point were determined by means of a highly sensitive differential scanning calorimeter (DSC 3100S manufactured by Bruker AXS).

|  | Melting Point | Glass Transition Point |
|---|---|---|
| Compound of Invention Example 1 | 352° C. | 138° C. |
| Compound of Invention Example 2 | 283° C. | 134° C. |

The compounds of the invention show a glass transition point of 100° C. or higher, and thus are stable in a thin-film state.

EXAMPLE 4

Using each of the compounds of the invention, a deposited film having a film thickness of 100 nm was prepared on an ITO substrate and work function was measured on a photoelectron spectroscopy in air (Model AC-3, manufactured by Riken Keiki Co., Ltd.).

|  | Work Function |
|---|---|
| Compound of Invention Example 1 | 6.28 eV |
| Compound of Invention Example 2 | 6.28 eV |

Thus, the compounds of the invention have values deeper than a work function of 5.4 eV possessed by common hole-transporting materials such as NPD and TPD and have a large hole-blocking ability.

EXAMPLE 5

Figure 3:
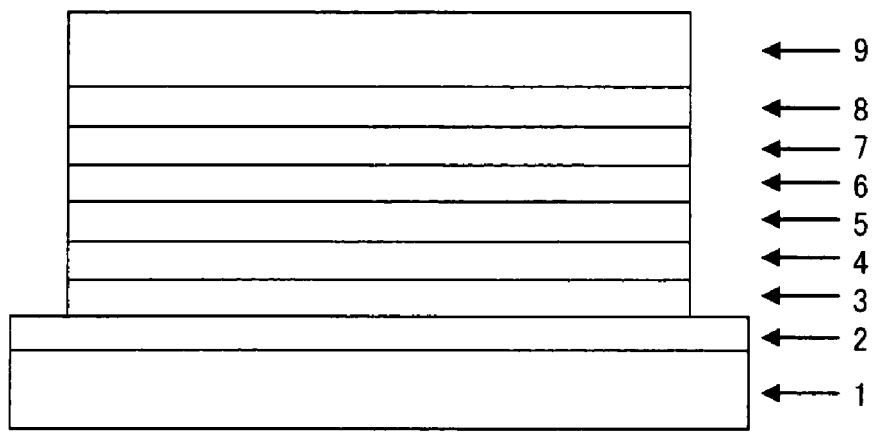
FIG. 3 is a drawing showing the constitution of the EL devices of Examples 5 to 7.
Figure 4:
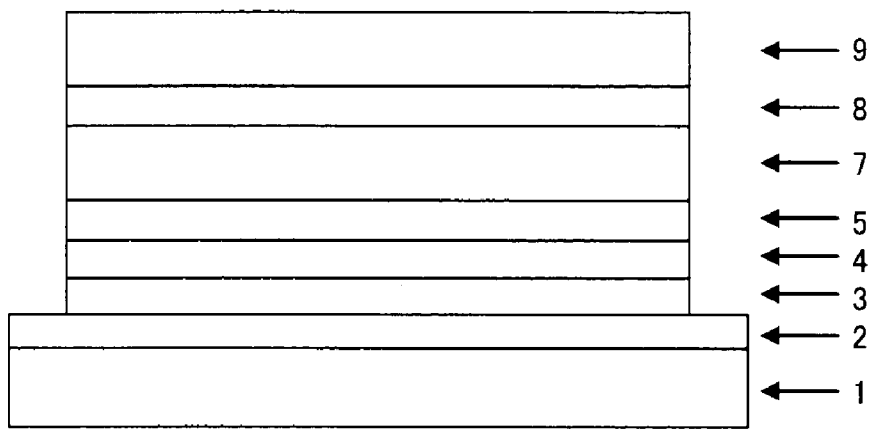
FIG. 4 is a drawing showing the constitution of the EL devices of Comparative Examples 1 and 2.

The organic EL device had a layered structure consisting of a hole-injecting layer 3, a hole-transporting layer 4, an emitting layer 5, a hole-blocking layer 6, an electron-transporting layer 7, an electron-injecting layer 8, and a cathode (aluminum electrode) 9 in this order on a glass substrate 1 on which an ITO electrode had been formed as a transparent anode 2 in advance, as shown in FIG. 3.

Specifically, after the glass substrate 1 on which ITO having a film thickness of 150 nm had been formed was washed with an organic solvent, the surface thereof was washed by UV ozone treatment. It was mounted in a vacuum deposition machine, which was then evacuated to 0.001 Pa or lower. Subsequently, copper phthalocyanine was formed thereon at a deposition rate of 3.6 nm/min to a thickness of about 20 nm as the hole-injecting layer 3. NPD was formed on the hole-injecting layer 3 at a deposition rate of 3.6 nm/min to a thickness of about 40 nm as the hole-transporting layer 4. As the emitting layer 5, $Alq_3$ was formed on the hole-transporting layer 4 at a deposition rate of 3.6 nm/min to a thickness of about 30 nm. On the emitting layer 5, the compound of Invention Example 1 (Compound 99) was formed at a deposition rate of 3.6 nm/min to a thickness of about 30 nm as the hole-blocking layer 6-cum-electron-transporting layer 7. On the hole-blocking layer-cum-electron-transporting layer 6 and 7, lithium fluoride was formed at a deposition rate of 0.36 nm/min to a thickness of about 0.5 nm as the electron-injecting layer 8. Finally, aluminum was deposited to a thickness of about 200 nm to form the cathode 9. Thus prepared device was stored in a vacuum desiccator and characteristic properties were measured in the atmosphere at ordinary temperature.

The results of measuring the luminescence properties when a current flowed at a current density of 20 mA/cm² to the organic EL device prepared by using the compound of Example 1 (Compound 99) of the invention are summarized in Table 1.

COMPARATIVE EXAMPLE 1

For comparison, an organic EL device was prepared under the same conditions as in Example 5 except that the material of the hole-blocking layer 6-cum-the electron-transporting layer 7 in Example 5 was replaced by $Alq_3$ as the electron-transporting layer 7. The results of measuring the luminescence properties when a current flowed at a current density of 20 mA/cm² to the prepared organic EL device are summarized in Table 1.

Furthermore, the emission initiation voltage was as low as 3.8 V in Example 5 as compared with 4.0 V for $Alq_3$.

Thus, the organic EL device of the invention has an excellent luminous efficiency and also achieves a remarkable reduction in the practical driving voltage, as compared with a device using $Alq_3$ used as a general electron-transporting material. From this, it could be found that the emission initiation voltage was also lowered.

EXAMPLE 6

In same manner as in Example 5, after the glass substrate 1 on which ITO having a film thickness of 150 nm had been formed was washed with an organic solvent, the surface thereof was washed by oxygen plasma treatment. It was set in a vacuum deposition machine, which was then evacuated to 0.001 Pa or less. Subsequently, the compound 129 as shown below was formed thereon as the hole-injecting layer 3 at a vapor deposition rate of 6.0 nm/min to a thickness of about 20 nm to cover the transparent anode 2. On the hole-injecting layer 3, the compound 130 as shown below was formed as the hole-transporting layer 4 at a vapor deposition rate of 6.0 nm/min to a thickness of about 40 nm. On the hole-transporting layer 4, the compound 131 as shown below and the compound 132 as shown below were formed as the emitting layer 5 to a thickness of about 30 nm by dual vapor deposition at a vapor deposition rate (Compound 131; 0.48 nm/min and Compound 132; 9.12 nm/min) such that the vapor deposition rate ratio of the compound 131: the compound 132 was 5:95. On the emitting layer 5, the compound of Example 1 (Compound 99) of the invention was formed as the hole-blocking layer 6-cum-the electron-transporting layer 7 at a vapor deposition rate of 6.0 nm/min to a thickness of about 30 nm. On the hole-blocking layer-cum-the electron-transporting layer 6 and 7, lithium fluoride was formed as the electron-injecting layer 8 at a vapor deposition rate of 0.6 nm/min to a thickness of about 0.5 nm. Finally, aluminum was vapor-deposited to a thickness of 150 nm to form the cathode 9. The prepared device was subjected to measurement of characteristic properties by applying a direct current voltage in the atmosphere at ambient temperature.

The results of the luminescence properties measurements when a current flowed at a current density of 10 mA/cm² through the organic EL device prepared using the compound of Invention Example 1 (Compound 99) are summarized in Table 2.

TABLE 1

| | Compound | Voltage [v] (@20 mA/cm²) | Luminance [cd/m²] (@20 mA/cm²) | Luminous efficiency [cd/A] (@20 mA/cm²) | Power efficiency [lm/W] (@20 mA/cm²) |
|---|---|---|---|---|---|
| Example 5 | Compound 99 | 6.90 | 927 | 4.64 | 2.11 |
| Comparative Example 1 | $Alq_3$ | 7.20 | 923 | 4.62 | 2.02 |

[Chem. 129]
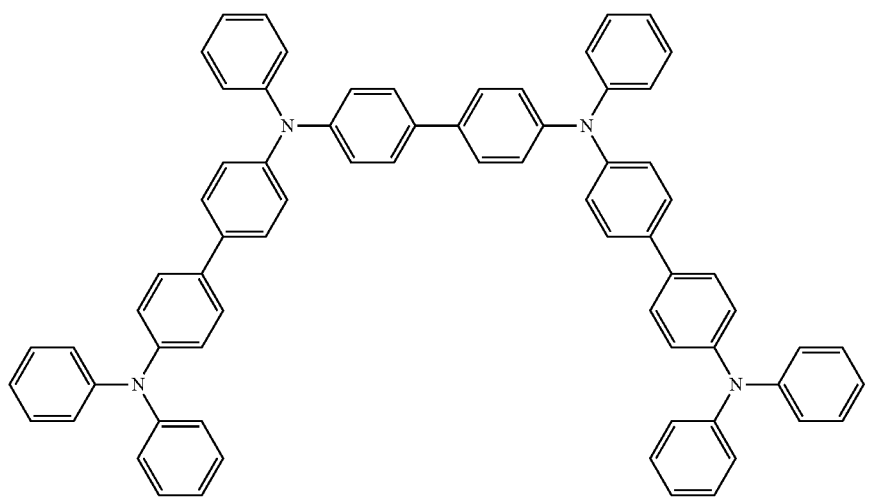
(Compound 129)
[Chem. 130]
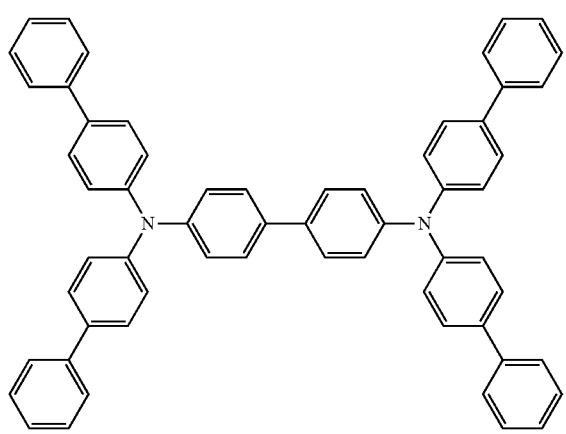
(Compound 130)
[Chem. 131]
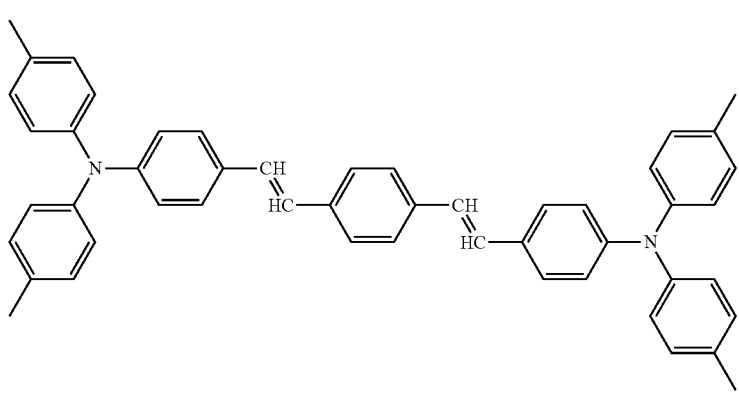
(Compound 131)

[Chem. 132]

(Compound 132)

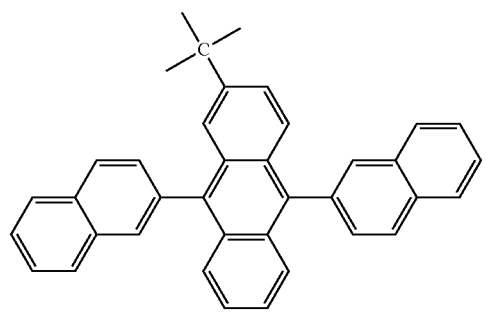

EXAMPLE 7

An organic EL device was prepared in the same manner as in Example 6, except that the compound of Example 2 (Compound 126) of the invention was used as the hole-blocking layer 6-cum-the electron-transporting layer 7. The results of the luminescence properties measurements when a current flowed at a current density of 10 mA/cm² through the prepared organic EL device are summarized in Table 2.

COMPARATIVE EXAMPLE 2

For comparison, an organic EL device was prepared under the same conditions as in Example 6, except that the material of the hole-blocking layer 6-cum-the electron-transporting layer 7 used in Example 6 was replaced by $Alq_3$ as an electron-transporting layer 7, and the characteristic properties thereof were investigated. The measurement results are summarized in Table 2.

and the power efficiency, when a current flowed at a current density of 10 mA/cm², were greatly improved.

Thus, it could be found that the organic EL device of the invention has an excellent luminous efficiency and a power efficiency, and also achieves remarkable reduction in the practical driving voltage as compared with a device using $Alq_3$ used as a general electron-transporting material.

While the invention has been described in detail and with reference to specific embodiments thereof, it will be apparent to one skilled in the art that various changes and modifications can be made therein without departing from the spirit and scope thereof.

The present application is based on Japanese Patent Application No. 2008-020110 filed on Jan. 31, 2008, and the contents are incorporated herein by reference.

Industrial Applicability

Since the compound having a substituted pyridyl group and a pyridoindole ring structure linked through a phenylene

TABLE 2

|  | Compound | Voltage [v] (@10 mA/cm²) | Luminance [cd/m²] (@10 mA/cm²) | Luminous efficiency [cd/A] (@10 mA/cm²) | Power efficiency [lm/W] (@10 mA/cm²) |
| --- | --- | --- | --- | --- | --- |
| Example 6 | Compound 99 | 5.00 | 885 | 8.85 | 5.60 |
| Example 7 | Compound 126 | 4.25 | 1140 | 11.40 | 8.45 |
| Comparative Example 2 | $Alq_3$ | 5.80 | 820 | 8.25 | 4.40 |

As shown in Table 2, the driving voltages when a current flowed at a current density of 10 mA/cm² were all low (Compound 99: 5.00 V and Compound 126: 4.25 V) with the compounds of Invention Example 1 and Example 2 (Compound 99 and Compound 126) as compared with 5.80 V of $Alq_3$. Further, all of the luminance, the luminous efficiency group according to the invention exhibits a good electron-injecting property and an excellent hole-blocking ability, and is stable in a thin-film state, it is excellent as a compound for an organic EL device. By preparing organic EL devices using the compound, driving voltage can be reduced and durability can be improved. For example, it becomes possible to spread the compound onto applications of electric home appliances and illuminations.

The invention claimed is:

1. A compound of formula (1):

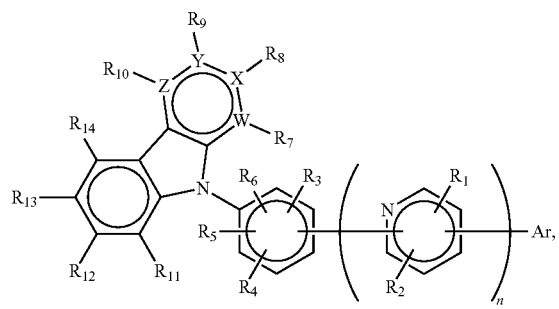

(1)

wherein

Ar is a substituted or unsubstituted aromatic hydrocarbon group, a substituted or unsubstituted aromatic heterocyclic group, or a substituted or unsubstituted condensed polycyclic aromatic group;

$R_1$ to $R_{14}$ are, independently, a hydrogen atom, a fluorine atom, a chlorine atom, a cyano group, a trifluoromethyl group, a linear or branched alkyl group comprising 1 to 6 carbon atoms, a substituted or unsubstituted aromatic hydrocarbon group, a substituted or unsubstituted aromatic heterocyclic group, or a substituted or unsubstituted condensed polycyclic aromatic group, n is 2 or 3, and W, X, Y, and Z are, respectively, a carbon atom or a nitrogen atom, provided that only one of W, X, Y, and Z is a nitrogen atom, and the nitrogen atom does not have the substituent $R_7$, $R_8$, $R_9$, or $R_{10}$.

2. The compound of claim 1, wherein n is 3.

3. The compound of claim 1, wherein n is 2.

4. An organic electroluminescent device, comprising:
a pair of electrodes; and
an organic layer interposed between the electrodes,
wherein the organic layer comprises the compound of claim 1.

5. The device of claim 4, wherein n in the compound of formula (1) is 3.

6. The device of claim 4, wherein n in the general formula (1) is 2.

7. The device of claim 4, wherein the organic layer comprises an electron-transporting layer and the electron-transporting layer comprises the compound of formula (1).

8. The device of claim 4, wherein the organic layer comprises a hole-blocking layer and the hole-blocking layer comprises the compound of formula (1).

9. The device of claim 4, wherein the organic layer comprises an emitting layer and the emitting layer comprises the compound of formula (1).

10. The device of claim 4, wherein the organic layer comprises an electron-injecting layer and the electron-injecting layer comprises the compound of formula (1).

11. The compound of claim 1, having a formula (2):

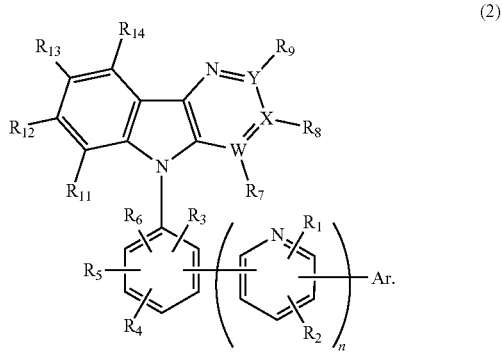

(2)

12. The compound of claim 1, having a formula (3):

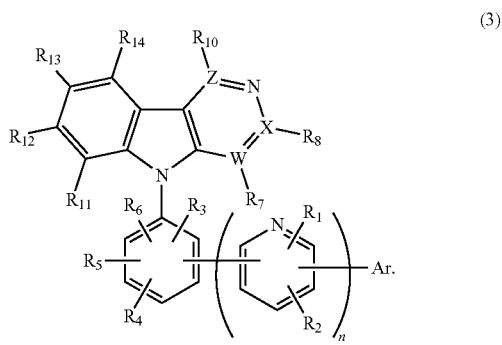

(3)

13. The compound of claim 1, having a formula (4):

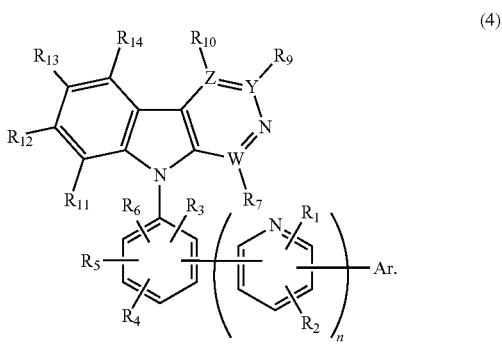

(4)

14. The compound of claim 1, having a formula (5):
(5)
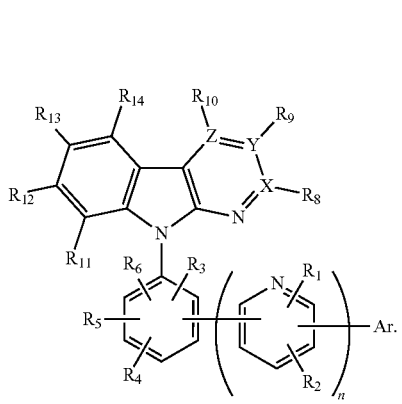
15. The compound of claim 1, having a formula (6):
(6)
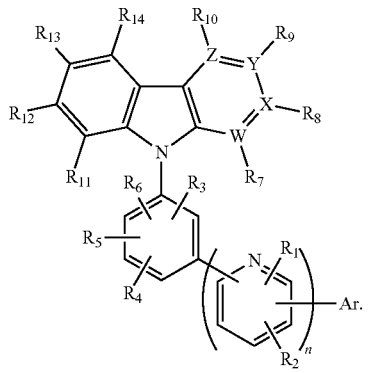
16. The compound of claim 1, having a formula (7):
(7)
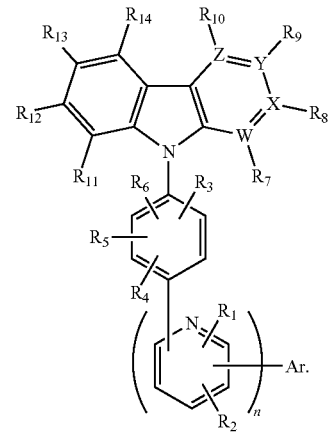
17. A compound selected from the group consisting of:
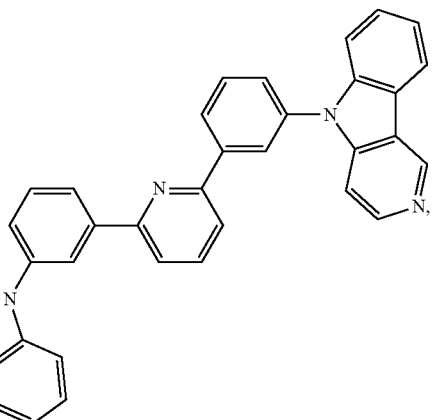
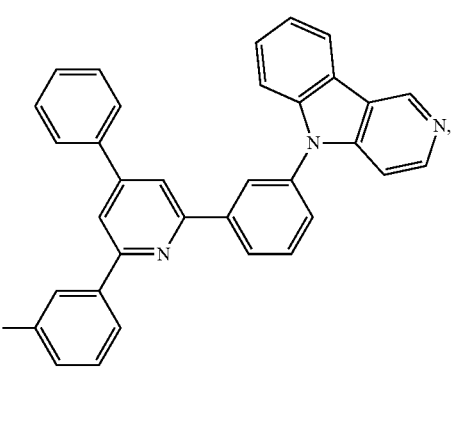

-continued

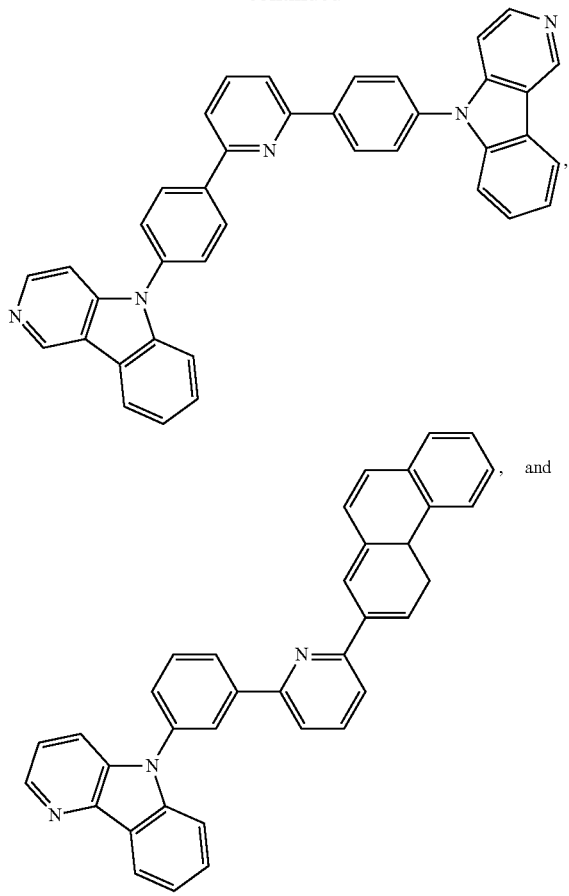

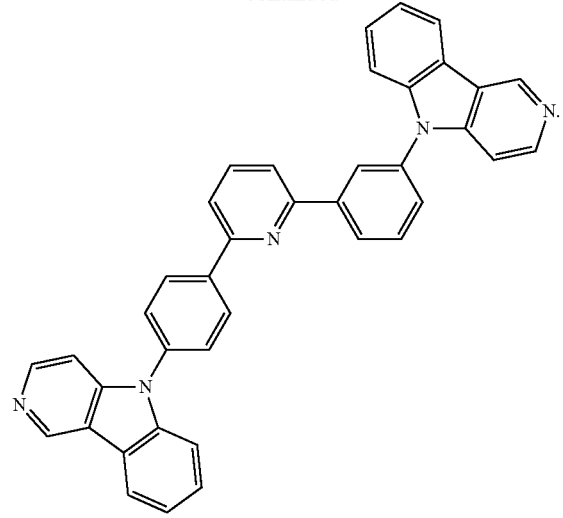

18. An organic electroluminescent device, comprising:
    a pair of electrodes; and
    an organic layer interposed between the electrodes,
    wherein the organic layer comprises the compound of claim 17.

19. The device of claim 18, wherein the organic layer comprises a hole-blocking layer and the hole-blocking layer comprises the compound.

20. The device of claim 18, wherein the organic layer comprises a layer which is at least one of
    an electron-transporting layer, an emitting layer, and an electron-injecting layer, and
    the layer comprises the compound.

* * * * *